US010183038B2

(12) United States Patent
Fornoni et al.

(10) Patent No.: US 10,183,038 B2
(45) Date of Patent: Jan. 22, 2019

(54) METHOD FOR PREVENTING AND TREATING RENAL DISEASE

(71) Applicant: L & F Research LLC, Miami, FL (US)

(72) Inventors: Alessia Fornoni, Coral Gables, FL (US); Sandra Merscher-Gomez, Miami, FL (US)

(73) Assignee: L&F Research LLC, Miami, FL (US)

( * ) Notice: Subject to any disclaimer, the term of this patent is extended or adjusted under 35 U.S.C. 154(b) by 123 days.

(21) Appl. No.: 14/967,831

(22) Filed: Dec. 14, 2015

(65) Prior Publication Data

US 2016/0220600 A1   Aug. 4, 2016

Related U.S. Application Data

(62) Division of application No. 13/879,892, filed as application No. PCT/US2011/056272 on Oct. 14, 2011, now Pat. No. 10,052,345.

(60) Provisional application No. 61/481,485, filed on May 2, 2011, provisional application No. 61/394,532, filed on Oct. 19, 2010.

(51) Int. Cl.
| *A61K 31/721* | (2006.01) |
| *A61K 45/06* | (2006.01) |
| *A61K 31/724* | (2006.01) |
| *C12Q 1/6897* | (2018.01) |
| *G01N 33/50* | (2006.01) |
| *G01N 33/569* | (2006.01) |
| *A61K 38/17* | (2006.01) |
| *A61K 39/395* | (2006.01) |

(52) U.S. Cl.
CPC ........ *A61K 31/724* (2013.01); *A61K 38/1774* (2013.01); *A61K 39/3955* (2013.01); *A61K 45/06* (2013.01); *C12Q 1/6897* (2013.01); *G01N 33/5044* (2013.01); *G01N 33/5091* (2013.01); *G01N 33/56966* (2013.01); *G01N 2800/245* (2013.01); *G01N 2800/347* (2013.01); *G01N 2800/50* (2013.01)

(58) Field of Classification Search
CPC .............. A61K 31/724; A61K 38/1774; A61K 39/3955; A61K 45/06; G01N 33/5044; G01N 33/56966; G01N 2800/245; G01N 2800/347; G01N 2800/50; C12Q 1/6897
USPC ......................................................... 514/58
See application file for complete search history.

(56) References Cited

U.S. PATENT DOCUMENTS

| 5,132,298 A | 7/1992 | Ueno |
| 6,890,549 B2 | 5/2005 | Artiss et al. |
| 7,276,351 B2 | 10/2007 | Teich et al. |
| 8,101,201 B2 | 1/2012 | Artisa |
| 8,202,702 B2 | 6/2012 | Neilson et al. |
| 8,263,413 B1 | 9/2012 | Hansen |
| 8,586,076 B2 | 11/2013 | Artiss et al. |
| 8,975,241 B2 | 3/2015 | Han |
| 9,326,539 B2 | 5/2016 | Artiss et al. |
| 2003/0133904 A1 | 7/2003 | Dagan et al. |
| 2004/0121983 A1 | 6/2004 | Chattopadhyay et al. |
| 2006/0148721 A1* | 7/2006 | Erondu ................ A61K 31/353 514/23 |
| 2007/0197438 A1 | 8/2007 | Reiser et al. |
| 2007/0292837 A1 | 12/2007 | Deutsch et al. |
| 2009/0324624 A1 | 12/2009 | Shibata |
| 2010/0184809 A1 | 7/2010 | Kremoser |
| 2010/0189653 A1 | 7/2010 | Robbins et al. |
| 2011/0314423 A1 | 12/2011 | Belotti et al. |
| 2012/0196831 A1 | 8/2012 | Han |
| 2012/0251527 A1 | 10/2012 | Reiser |

FOREIGN PATENT DOCUMENTS

| EP | 1 125 584 A1 | 8/2001 |
| EP | 1125584 A1 | 8/2001 |
| JP | 2004323443 A | 11/2004 |
| JP | 2008523096 A | 7/2008 |
| JP | 2008528610 A | 7/2008 |
| JP | 2009298820 A | 12/2009 |
| JP | 2010508372 A | 3/2010 |
| JP | 2012505251 A | 3/2012 |
| WO | WO 97/10828 A1 * | 3/1997 ............. A61K 31/70 |
| WO | 2006071491 A1 | 7/2006 |

(Continued)

OTHER PUBLICATIONS

The Merck Manual, 1992, pp. 1700-1702.*
Delville et al, J. Am. Soc. Nephrol., 2016, 27, 2520-2527.*
Adelman et al, J. Pediatr. 2001, 138, 481-485.*
Yancey et al, The Journal of Biological Chemistry, 1996, 271(27), 16026-16034.*
Gohh et al, Am. J. Transplantation, 2005, 5, 2907-2912.*
English-language translation of Chinese Office Action, dated Feb. 5, 2016.
Atger, V. M. et al."Cyclodextrins as catalysts for the removal of cholesterol from macrophage foam cells." J. Clin. Invest. 99, 773 780 (1997).

(Continued)

*Primary Examiner* — Ganapathy Krishnan
(74) *Attorney, Agent, or Firm* — Millen, White, Zelano & Branigan, PC

(57) ABSTRACT

Assays, methods and kits for predicting a subject's (e.g., human) risk of primary glomerulopathy, secondary glomerulopathy or recurrence (e.g., post-transplant recurrence) of any glomerular disease include examining cells for the presence or absence of cytoskeletal disruptions or rearrangements and examining cells for modulation of expression and/or activity of markers such as SMPDL-3b. Assays for predicting if a diabetic subject will develop kidney disease or a patient with FSGS will develop recurrent disease after transplant also include examining cells for the presence or absence of cytoskeletal disruptions or rearrangements and examining cells for modulation of expression and/or activity of markers such as SMPDL-3b. Also described herein are compositions and methods for treating and preventing the aforementioned disorders.

11 Claims, 9 Drawing Sheets

(56) References Cited

FOREIGN PATENT DOCUMENTS

| WO | 2006081363 A2 | 8/2006 |
| --- | --- | --- |
| WO | 2008055871 A1 | 5/2008 |
| WO | 2009142988 A2 | 11/2009 |
| WO | 2010042202 A1 | 4/2010 |
| WO | 2010042886 A2 | 4/2010 |
| WO | 2010054167 | 5/2010 |
| WO | 2011043630 A2 | 4/2011 |
| WO | 2012012473 A1 | 1/2012 |
| WO | 2012054321 | 4/2012 |
| WO | 2012054321 A2 | 4/2012 |

OTHER PUBLICATIONS

International Preliminary Report on Patentability and Written Opinion for PCT/US2013/036484 (issued by the International Bureau dated Oct. 23, 2014).
Camargo et al., "Cyclodextrins in the treatment of mouse model of Niemann-Pick disease", Life Sciences 70 (2): pp. 131-142 (2001)—Abstract only.
International Search Report dated Nov. 5, 2013 in WO 2013/155485 (Fornoni et al.) published Oct. 17, 2013, all pages.
Reiser et al., "Toward the development of podocyte-specific drugs", Kidney International, vol. 77, pp. 662-668, published online Feb. 3, 2010.
Saleem et al., "A conditionally immortalized human podocyte cell line demonstrating nephrin and podocin expression", Journal of the American Society of Nephrology, vol. 13, pp. 630-638, 2002.
Munkert et al., "Characterization of the transcriptional regulation of the human MT1-MMP gene and association to risk reduction for focal-segmental glomerulosclerosis with two functional promoter SNPs", Nephrology Dialysis Transplantation, vol. 24, pp. 735-742, 2009, published online Oct. 16, 2008.
Harendza et al., "The transcriptional regulation of podocin (NPHS2) by Lmx1b and a promoter single nucleotide polymorphism", Cellular & Molecular Biology Letters, vol. 14, pp. 679-691, Jun. 27, 2009.
Perosa et al., "Generation of biologically active linear and cyclic peptides has revealed a unique fine specificity of rituximab and its possible cross-reactivity with acid sphingomyelinase-like pohophodiesterase 3b precursor", Blood, vol. 107, No. 3, pp. 1070-1077, Feb. 2006.
Moeller et al., "Two gene fragments that direct podocyte-specific expression in transgenic mice", Journal of the American Society of Nephrology, vol. 13, pp. 1561-1567, 2002.
Delville et al., "B7-1 blockade does not improve post-transplant nephrotic syndrome caused by recurrent FSGS", Journal of the American Society of Nephrology, doi: 10, 1681/ASN.2015091002, pp. 1/8-8/8, 2015.
GenBank Accession No. NM_001009568, 1, GI: 57242799, publicly available Jul. 2010.
GenBank Accession No. NM_014474.2, GI: 57242797, publicly available Jul. 1010.
Coward et al., "Nephrotic plasma alters slit diaphragm-dependent signaling and translocates nephrin, podocin, and CD2 associated protein in cultured human podocytes", Journal of the American Society of Nephrology: JASN, vol. 16, No. 3, pp. 629-637, Jan. 19, 2005.
Alam et al., Chapter 6, "Reporter gene for monitoring expression in mammalian cells, S.C. Makrides (Ed.) in Gene Transfer and Expression in Mammalian Cells", Elsevier Science B.V., pp. 291-308, 2003.
Cormack-Aboud et al., "Rosuvastatin protects against podocyte apoptosis in vitro", Nephrology, Dialysis, Transplantation, vol. 24, pp. 404-412, 2009 (advanced access publication Sep. 27, 2008).
Society News: 2009 Archives. American Society of Nephrology, Society News—2009 Archives, printed from http://www.asn-online.org/news/2009/ as p. 1/1 on Jun. 3, 2015.
Bijian et al., "Actin cytoskeletoon regulates extracellular matrix-dependent survival signals in glomerular epithelial cells", American Journal of Physiology, vol. 289, pp. F1313-F1323, 2005.
Sun et al., "Glomerular transcriptome changes associated with lipopolysaccharide-induced proteinuria", American Journal of Nephrology, vol. 29, pp. 558-570, Jan. 9, 2009.
Reiser et al., "Regulation of mouse podocyte process dynamics by protein tyrosine phosphatases", Kidney International, vol. 57, pp. 2035-2042, 2000.
Srivastava et al., LPS and PAN-induced podocyte injury in an in vitro model of minimal change disease: changes in TLR profile, Journal of Cell Communications and Signaling, vol. 7, pp. 49-60, Nov. 2013.
Ahem. Biochemical, reagents kits offer scientists god return on investment, The Scientist, vol. 9 No. 15, pp. 20, Jul. 1995, printed as pages 1/7-7/7.
Hattori et al., "Increase of integrin-linked kinase activity in cultured podocytes upon stimulation with plasma from patients with recurrent FSGS", American Journal of Transplantation, vol. 8, pp. 1550-1556, 2008.
Chen et al., "Visualize circulating factor by using podocytes as target cell in patients with FSGS", Presented at the Ameerican Society of Nephrology meeting (Oct. 30, 2009) San Diego, CA (abstract only).
Collino et al., "Preeclamptic sera induce nephrin shedding from podocytes through endothelin-1 release by endothelial golmerular cells", Am J. Physical Renal Physical (Feb. 2008), vol. 294, pp. F1185-F1194.
Doublier et al., "Nephrin redistribution on podocytes is a potential mechanism for proteinuria in patients with primary acquired nephrotic syndrome", Am J Pathology (May 2001), vol. 156, pp. 1723-1731.
Fornoni et al., "Efffect of Ritusimab on the regulation of sphingomyelinase-like phosphodiesterase 3b-precursor in recurrent FSGS", ASN Renal Week, San Diego (Nov. 2009): Abstract No. 552231 (3 pages).
Fornoni et al., "Rituximab affects podocytes in recurrent FSGS via sphingomyelination", Poster International Podocyte Meeting (Jun. 2010) Bristol, UK (1 page).
Letavernier et al, "mToR inhibitors-induced proteinuria: Mechanisms, significance, and management", Transplanation Reviews, (2008), vol. 22, pp. 125-130.
Sageshima et al., "Rituximab may decrease the incidence of FSGS recurrence after kidney transplantation (KT) by preventing down regulation of sphingomyelinase-like phosphodiesterase 3b-precursor (SMLPD-3b) in the podocyte", American Transplant Society meeting, San Diego, (May 2010): Abstract No. 252551 (2 pages).
Fornoni et al., "Rituximab targets podocytes in recurrent focal segmental glomerulosclerosis", Sci. Transl. Med. (Jun. 2011), vol. 3, 85ra46, pp. 1-10.
Extended European Search Report dated Jun. 29 2016, issued in corresponding European Application No. 13775223, 11 pages.
Wijesekara, N. et al., "miR-33a Modulates ABCA1 Expression, Cholesterol Accumulation, and Insulin Secretion in Pancreatic Islets", Diabetes, XP055248061, vol. 61, No. 3, Feb. 7, 2012, pp. 653-658.
Tang, C. et al., "Diabetes reduces the cholesterol exporter ABCA1 in mouse macrophages and kidneys", Journal of Lipid Research, XP055268069, vol. 51, No. 7, Jul. 1, 2010, pp. 1719-1728.
Kilsdonk E. P. C. et al., "Cellular Cholesterol Efflux Mediated by Cyclodextrins", Journal of Biological Chemistry, American Society for Biochemistry and Molecular Biology, XP001146317, vol. 270, No. 29, Jul. 21, 1995, pp. 17250-17256.
Hideki, Ozasa. et al., "Pioglitazone enhances cholesterol efflux from macrophages by increasing ABCA1/ABCG1 expressions via PPARγ/LXRα pathway: findings from in vitro and ex vivo studies" Atherosclerosis, Elsevier Ireland Ltd, IE, vol. 219, No. 1, Jul. 25, 2011, pp. 141-150, ISSN: 0021-9150.
Chapman, J. M., "Pitavastatin: novel effects on lipid parameters" Atheroscler Suppl. Nov. 2011;12(3):277-84.
Merscher-Gomez S, "Cyclodextrin protects podocytes in diabetic kidney disease", Diabetes. Nov. 2013; 62(11):3817-27.

(56) References Cited

OTHER PUBLICATIONS

Tufro A, "Cholesterol accumulation in podocytes: a potential novel targetable pathway in diabetic nephropathy", Diabetes. Nov. 2013; 62(11):3661-2.
Hristea et al., "Successful treatment of recurrent focal segmental glomerulosclerosis after kidney transplantation by plasmapheresis and rituximab" Transplant International.Jan. 2007 ; vol. 20, Issue 1, pp. 102-105.
Park et al. "Investigation of toxic metabolites during drug development," Toxicol Appl Pharmacol. Sep. 1, 2005;207(2 Suppl):425-34.
Camargo et al., "Cyclodextrins in the treatment of mouse model of Niemann-Pick disease", Life Sciences 70 (2): pp. 131-142 (2001).
Spino et al., "Changing the Paradigm for the Treatment and Development of New Therapies for FSGS" Front Pediatr. Mar. 2016; 4: 25.
Pullen et al.,"Drug discovery in focal and segmental glomerulosclerosis." Kidney Int. Jun. 2016;89(6):1211-20. (Epub Apr. 23, 2016.).
Search Report dated Jan. 10, 2017, issued in corresponding Canadian Application No. 2852904 (7 pages).
Fornoni et al., Abstract TH-FC048, Renal Week 2009, American Society of Nephrology, San Diego, CA, USA; available online at the "Renal Week 2009 Abstract Supplement (PDF)" , p. 12A (under "Archives 2009-2003"): downloaded from http://www.asn-online.org/abstracts/ on Jan. 26, 2017.
Shi SF, Wang SX, Zhang YK, et al. Ultrastructural features and expression of cytoskeleton proteins of podocyte from patients with minimal change disease and focal segmental glomerulosclerosis, Ren Fail , 2008, vol. 30 (p. 477-483).
Barisoni L. et al., J Am Soc Nephroi, vol. 10, pp. 51-61, Jan. 1999 (Jan. 1999).
Faul C. et al., Nat Med., vol. 14, pp. 931-938, Sep. 2008 (Sep. 2008).
Machine translation of JP2004323443A published Nov. 18, 2004 to Tokai Univ.
Office Action in corresponding JP Appln. No. 2015-505963 dated Jan. 31, 2017.
Yancey, P. et al., The Journal of Biological Chemistry, vol. 271, No. 27, pp. 16026-16034, published on Jul. 5, 1996.
Englsih language translation of Office Action in corresponding Chinese Application No. 2013800198675 dated Apr. 20, 2017.
Office Action in corresponding CN Application No. 201380019867.5 dated Nov. 1, 2017.
Office Action in co-pending U.S. Appl. No. 14/391,236 dated Nov. 27, 2017.
Yun, J et al "Possible anti-obesity therapeutics from nature—A review" Phytochemistry 71 (2010) 1625-1641.

Jiang, T et al "Farnesoid X Receptor Modulates Renal Lipid Metabolism, Fibrosis, and Diabetic Nephropathy" Diabetes, vol. 56, Oct. 2007 (2485-2493).
Kambham, N et al. "Obesity-related glomerulopathy: an emerging epidemic." Kidney Int. Apr. 2001;59(4):1498-509.
Morales, E et al. "Beneficial effects of weight loss in overweight patients with chronic proteinuric nephropathies." Am J Kidney Dis. Feb. 2003;41(2):319-27.
Office Action in corresponding JP Application No. MX/a/2014/012200 dated Sep. 5, 2017.
English language translation of Office Action in corresponding Application No. 2 0 1 5-5 0 5 9 6 3 dated Aug. 9, 2017.
Kilsdonk E P C, et al.: "Cellular cholesterol efflux mediated by cyclodextrins" Journal of Biological Chemistry, American Society for Biochemistry and Molecular Biology, US, vol. 270, No. 29, Jul. 21, 1995 (Jul. 21, 1995), pp. 17250-17256, ISSN: 0021-9258.
Tae-Hyun Yoo : "Sphingomyelinase-Like Phosphodiesterase 3b Expression Levels Determine Podocyte Injury Phenotypes in Glomerular Disease" Journal of the American Society of Nephrology, vol. 26, pp. 133-147, 2015, Epub Jun. 12, 2014. (Year: 2014).
Trimarchi, H. Abatacept and glomerular diseases: The open road for the second signal as a new target is settled down. Recent Patents on Endocrine, Metabolic & Immune Drug Discovery, vol. 9,pp. 2-14, 2015. (Year: 2015).
PTO Form 892 from corresponding copending U.S. Appl. No. 13/879,892 dated Dec. 27, 2017.
English translation of Office Action in corresponding JP application No. 2015-505963 dated Apr. 10, 2018.
Frijlink: Pharmaceutical Research, 1991, 8 (1), p. 9-16.
English translation of Office Action in corresponding CN application No. 2013-80019867.5 dated May 8, 2018.
Office Action in corresponding MX application No. 2014-012200 dated Mar. 1, 2018 and translation thereof.
Christian A., Use of cyclodextrins for manipulating cellular cholesterol content, J Lipid Res. Nov. 1997;38(11):2264-72.
Office Action in corresponding copending U.S. Appl. No. 13/879,892 dated Dec. 27, 2017.
Foreign Office Action in corresponding European application No. 13 775 223.4 dated Jul. 31, 2018.
Office Action in co-pending U.S. Appl. No. 14/391,236 dated May 30, 2018.
Notice of Allowance and form PTO-892 in copending U.S. Appl. No. 14/391,236 dated Sep. 20, 2018.
Zhang Y. et al. "Activation of the nuclear receptor FXR . . . " PNAS vol. 103, No. 4, pp. 1006-1011 (2006).
Office Action in corresponding MX/a/2014/0122200 dated Aug. 16, 2018 (pp. 1-5) and translated English summary of same.
Office Action in corresponding CN application 201380019867.5 dated Sep. 28, 2018 (pp. 1-5) and translated English summary of relevant portion.

* cited by examiner

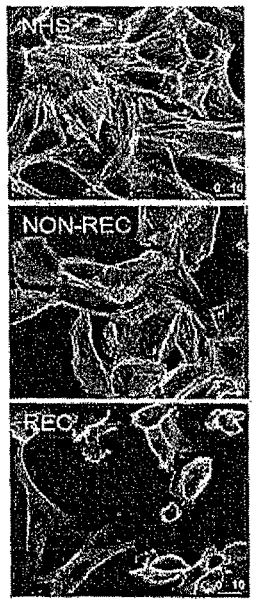
Fig. 1A
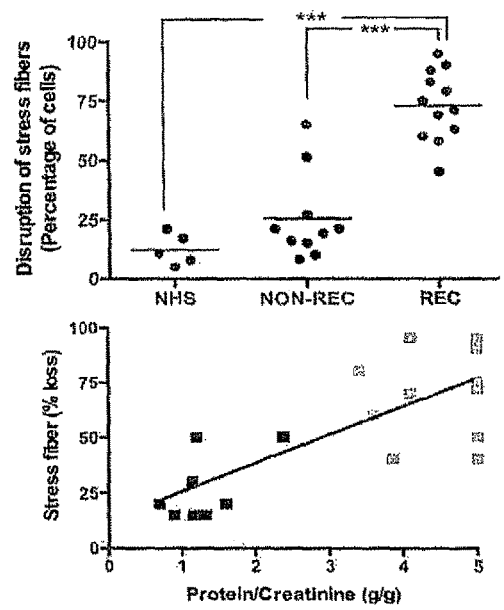
Fig. 1B
Fig. 1C
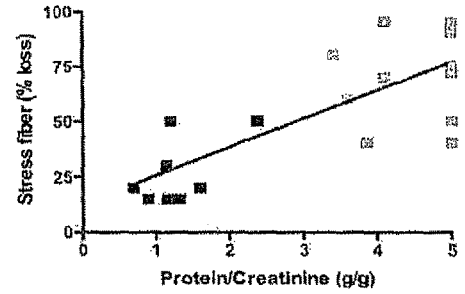
Fig. 1D
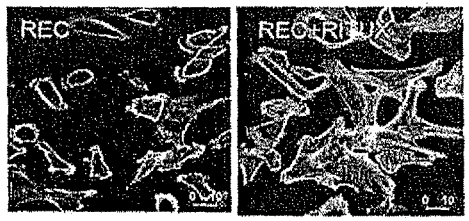
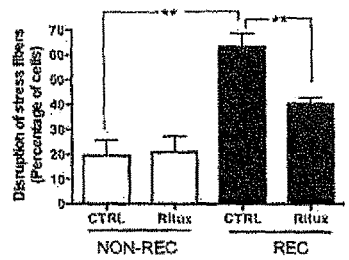
Fig. 1E
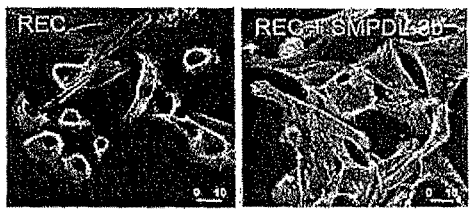
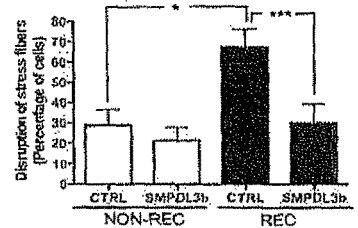

Fig. 3A
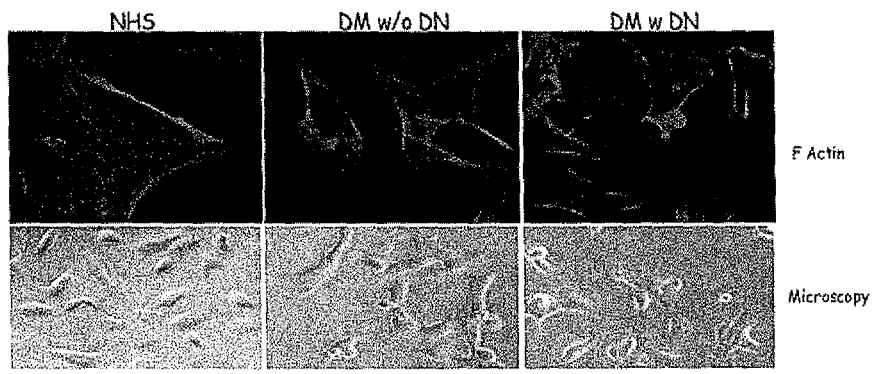
Fig. 3B
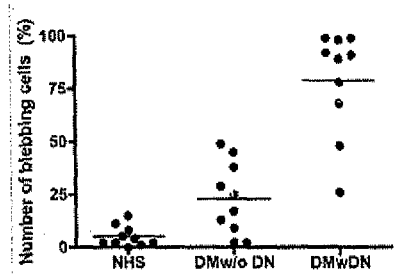
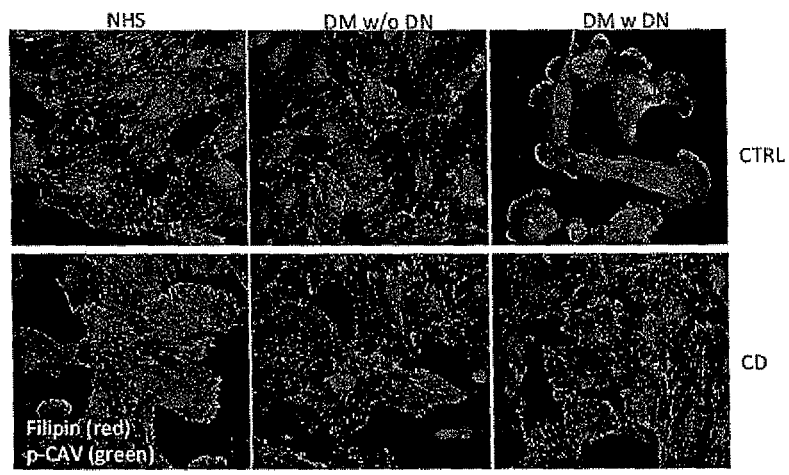
Fig. 3C

METHOD FOR PREVENTING AND TREATING RENAL DISEASE

CROSS-REFERENCE TO RELATED APPLICATIONS

This application is a U.S. Divisional application Ser. No. 13/879,892 filed Apr. 17, 2013, which is a 371 National Stage Application of International Application No. PCT/US11/56272, filed Oct. 14, 2011, which claims priority to U.S. Provisional Application No. 61/481,485, filed May 2, 2011, and U.S. Provisional Application No. 61/394,532, filed Oct. 19, 2010, the entireties of which are incorporated herein by reference.

FIELD OF THE INVENTION

The invention relates generally to the fields of cellular biology, molecular biology, nephrology, medicine and transplantation.

BACKGROUND

Presently, there is no predictive test for the development of glomerular disorders, and diagnosis is based on kidney biopsies, a very invasive diagnostic procedure. As an example, there is no predictive test for recurrent focal segmental glomerulosclerosis (FSGS) after a kidney transplant. FSGS accounts for up to 20% of end-stage renal disease (ESRD) and is the most common progressive glomerular disorder affecting the pediatric population. Although renal transplantation remains the best treatment option for patients with FSGS reaching ESRD, recurrent FSGS after transplantation occurs in 30-70% of the patients and markedly affects graft survival. The ability to predict which patients are at high risk for recurrent disease remains a challenge. As a second example, although 20-40% of patients with diabetes will develop diabetic nephropathy (DN), the identification of those patients at risk remains elusive.

The ability to predict the development of proteinuria and glomerular disorder in any primary or systemic illnesses that can affect the kidney is elusive (e.g., lupus, HIV, hepatitis, hemathological disorders, sarcoidosis). Similarly, no methodology exists for predicting if family members of patients with a non-genetic proteinuric glomerular disorder are at risk to develop the disorder. A prediction assay is also lacking for patients undergoing a kidney transplant to determine the risk for the development of kidney disease after kidney transplant (e.g., transplant glomerulopathy, rejection, allograft nephropathy, recurrence of the primary disease). Furthermore, for any renal (kidney) disease and/or glomerulopathy that can be either idiopathic (e.g., Membranous, minimal change, IgA, Membranoproliferative, FSGS, paucimmune glomerulonephritis), genetic (e.g., FSGS, storage disorders, Alport's) or secondary to a systemic illness (e.g., lupus, diabetes, HIV, hepatitis, hemathological disorders, sarcoidosis, other autoimmune disorders), the ability to predict what are the better treatment strategies for a specific patient is unrealized.

Proteinuria, kidney injury, renal failure and renal-related conditions contribute significantly to morbidity and mortality of affected patients. Proteinuric renal failure and/or kidney injury is often the result of local or systemic illnesses that affect the function of key elements of the glomerular filtration barrier of the kidney, a complex cellular structure that under physiological conditions prevents the leakage of protein from the blood side to the urinary side[1]. Although glomerular disease is the most common cause of pathological proteinuria, proteinuria can also be the result of tubular dysfunction or protein overflow. Among the three major components of the glomerular filtration barrier (endothelial cells, glomerular basement membrane and podocytes), the podocyte is a highly specialized cell that is usually affected in the early phases of proteinuric glomerular disorder as a result of diverse insults (e.g., systemic illnesses, autoimmune diseases, infectious diseases, toxic agents, drugs and others). These insults cause podocyte actin cytoskeleton remodeling and lead to clinically relevant proteinuria. Clinically relevant proteinuria is generally defined as urinary excretion of more than 150 mg of protein per 24 h or 150 mg/g creatinine on a spot urine sample or as urinary excretion of albumin of more than 30 mg per 24 h or 30 mg/g creatinine on a spot urine sample. Podocyte injury is also an important feature of DN, which is the most common cause of end stage renal disease in the United States. As proteinuric chronic kidney disease represents a growing epidemic despite available treatments, there is a need for the development of new drugs or of new indications for existing molecules and compounds.

SUMMARY

Assays, methods and kits for predicting a subject's (e.g., human) risk of primary glomerulopathy, secondary glomerulopathy or post-transplant recurrence of any glomerular disease (e.g., FSGS, DN, Membranous nephropathy, minimal change disease, IgA nephropathy, Membranoproliferative glomerulopathy, lupus nephritis, myeloma kidney, hypertensive nephrosclerosis, paucimmune glomerulonephritis, preeclampsia, amyloidosis, cryoglobulinemia, thrombotic thrombocytopenic purpura, Hemolytic uremic syndrome, scleroderma kidney, Alport's glomerulopathy, transplant glomerulopathy storage disorders and other rare genetic disorders) are described herein. Assays and methods described herein may be used to predict the development of glomerular renal disorders (e.g., development of albuminuria, proteinuria, clinical or histological evidence of any of the above conditions). Assays described herein may also allow for the identification of a therapeutic agent for preventing or treating glomerular diseases (e.g., FSGS, DN, Membranous nephropathy, minimal change disease, IgA nephropathy, Membranoproliferative glomerulopathy, lupus nephritis, myeloma kidney, hypertensive nephrosclerosis, paucimmune glomerulonephritis, preeclampsia, amyloidosis, cryoglobulinemia, thrombotic thrombocytopenic purpura, Hemolytic uremic syndrome, scleroderma kidney, Alport's glomerulopathy, transplant glomerulopathy, storage disorders and other rare genetic disorders). Such assays include high throughput screening assays (e.g., high throughput screening of libraries of compounds). Identification of patients at risk for kidney disease and in vitro determination of specific existing and new drugs to be utilized for each individual can be achieved using the assays and methods described herein, providing for the development of a personalized nephrology approach to diagnosis and treatment that may, for example, replace kidney biopsies. A specific kit for each glomerular and/or renal disorder can be provided in combination with a disease-specific set of drugs to be tested in vitro to predict a subject's response to treatment. As shown in FIGS. 1A, 1B, 1C, 1D, 1E, 2A, 2B, 2C, 2D, 2E, 2F, 2G, 3A, 3B, 3C, 3D, 3E, 3F, 4A, 4B and 4C, the assays, methods and kits described herein provide for the utilization of existing and approved drugs (e.g., drugs for off label use) with a personalized approach.

In one embodiment, the assays, methods and kits involve cultured human podocytes that display a disease-specific phenotype when contacted with a biological sample from a subject having or predisposed to the specific disease (e.g., FSGS, DN, etc.). In the case of FSGS, the presence of a soluble permeability factor (PF) in the serum of patients with high risk for recurrence (e.g., after kidney transplantation) has been shown: the presence of a PF above a preset range of activity is associated with a recurrence rate as high as 86%. However, the specific nature and function of PF remains unclear; even less clear is the existence of specific podocyte targets for recurrent disease, leading to podocyte malfunction and detachment, similar to what has been described in primary FSGS. In the experiments described herein, a translational approach to cell culture, where target cells of interest are studied after exposure to the sera of patients with a given disorder (instead of the traditional fetal bovine serum), has been applied to normal human podocytes cultured in the presence of the sera of 18 patients with FSGS collected immediately before transplantation and initiation of immunosuppression. Based on the actin cytoskeleton rearrangement that was observed by confocal microscopy, a quantitative assessment of a diseased phenotype has been established by counting the number of cells with disruption of stress fibers (the hallmark of a diseased phenotype for podocytes) among 100 cells being evaluated in adjacent fields (FIGS. 1A-1E). Further, a correlation between the modulation of SMPDL-3b and the degree of cell malfunction has been developed (Fornoni et al, Sci Transl Med vol. 3:85ra46, 2011), offering a bioassay that includes a more objective and quantitative assessment of risk (FIGS. 2A-2G). The development of a SMPDL-3b reporter podocyte or other transfectable mammalian cell line (e.g., HEK cell line) that allows for a direct correlation between a marker (e.g., luciferase activity) detected after exposure to patient sera in the presence or absence of a given drug and clinical outcome will offer a fast and more quantitative method predictive of clinical outcome. In this bioassay, data can be confirmed by Western blot and PCR as reported (Fornoni et al, Sci Transl Med vol. 3:85ra46, 2011), for example. As SMPDL-3b affects cellular metabolism, function, and survival, luciferase activity in cells exposed to patient sera are studied alone or in conjunction with determination of cellular lipid content, apoptosis, oxygen consumption rate and quantitative measures of oxidative stress (e.g., as determined by seahorse technology). The assays, methods and kits described herein provide a sensitive method to identify, prior to transplantation, those patients that are at risk for the development of recurrent FSGS or other glomerular disease, which in turn will affect the choice of therapeutic agents to be administered at time of transplantation to more or less aggressively prevent recurrent disease.

The experiments described herein additionally show that cell enlargement, blebbing and loss of stress fibers, lipid accumulation, modulation of SMPDL-3b and apoptosis are observed in normal podocytes exposed to the sera of diabetic patients with DN, but not in podocytes exposed to sera from normal non-diabetic controls or from diabetic patients without DN. Thus, the assays, kits and methods described herein provide for the screening of patients with diabetes for their risk to develop DN (FIGS. 3A and 3B). Advantageously, a specific kit for each glomerular disorder is provided in combination with a disease-specific set of drugs to be tested in vitro to predict a subject's response to treatment.

Methods for lowering plasma membrane and cellular cholesterol/lipids for the prevention, treatment, cure, or reversal of renal-related disorders by the use of cyclodextrin (CD), its derivatives or any other drug capable of lowering plasma membrane and cellular cholesterol/lipids, are also described herein. Strategies that reduce cellular cholesterol/lipids and that do not solely affect the cholesterol synthetic pathway (such as statins), but also the influx and efflux mechanisms leading to cholesterol/lipids accumulation, can be utilized for the prevention and cure of renal-related disorders. CD, its derivatives or any cellular cholesterol-lowering agent belonging to a class of compounds other than statins (such as chromium picolinate) are encompassed by the compositions and methods described herein. Such strategies also include the modulation of sphingolipid-related enzymes, as it was demonstrated in the experiments described below that sphingolipid-related proteins can modulate the cellular cholesterol content (FIGS. 5A and 5B). As accumulation of cellular cholesterol/lipids occurs with diabetes, aging, obesity and other chronic inflammatory diseases, and visceral cholesterol accumulation results in organ malfunction, cyclodextrin derivatives can be more broadly utilized for the prevention and the cure of these other medical conditions. Therefore, CD, its derivatives or any other drug that lowers plasma membrane or cellular accumulation of cholesterol/lipids may result in the prevention and cure for obesity and diabetes and may slow aging. In the example shown in FIGS. 6A and 6B, the following set of data was generated. Cholesterol depletion by intravenous injection of Hydroxypropyl-beta-cyclodextrin (CD) protects from Lipopolysaccharide (LPS) induced proteinuria (FIG. 6A) in mice and from LPS-induced intracellular signaling mediated by MyD88 in isolated glomeruli (FIG. 6B). Cholesterol depletion with Methyl-beta-cyclodextrin (CD) prevents several phenotypic changes observed in normal human podocytes exposed to the sera of patients with diabetic nephropathy. Those phenotypic changes include: cell blebbing, lipid accumulation, and cell apoptosis (FIGS. 3A-3F). As modulation of SMPDL-3b expression in podocytes leads to a modulation of lipids and lipid related proteins (such as ASMase, FIGS. 5A and 5B), modulation of SMPDL-3b results in a modulation of cellular lipid content that renders cells more or less susceptible to injury (FIGS. 5A and 5B).

Described herein is an assay for determining if at least one subject who is at risk for a primary or secondary proteinuric glomerular disorder or who has a primary or secondary proteinuric glomerular disorder is at risk for primary or secondary disease development, progression or recurrence of the proteinuric glomerular disorder after kidney transplantation. The assay includes: contacting a biological sample (e.g., blood, saliva, serum, plasma, tissue, and urine) from the at least one subject with a culture of human podocytes; examining the podocytes for the presence or absence of cytoskeletal disruptions or rearrangements resulting in determination of a phenotype of the podocytes; and correlating the presence of cytoskeletal disruptions or rearrangements with an increased risk of development, progression or recurrence of the proteinuric glomerular disorder after kidney transplantation in the subject. The proteinuric glomerular disorder (e.g., FSGS or diabetic nephropathy) is typically a primary proteinuric glomerular disorder, a secondary proteinuric glomerular disorder, or a post-transplant proteinuric glomerular disorder. The at least one subject can be a plurality (e.g., 2, 3, 4, 5, 10, 15, 20, 50, 100) of subjects who are at risk for a primary or secondary proteinuric glomerular disorder or who have a primary or secondary proteinuric glomerular disorder. The cytoskeletal disruptions or rearrangements can be examined by, for example, microscopy, Western blotting, ELISA, flow cytometry and reporter assays. In the assay, the phenotype can be compared to a negative control and a positive control. The assay can further include analyzing the phenotype quantitatively based on a standard curve generated with a dose-dependent chemical disruption of actin cytoskeleton. By using the assay, for the at least one subject who is at risk for a primary, secondary or recurrent proteinuric glomerular disorder or who has a primary, secondary or recurrent proteinuric glomerular disorder, a personalized treatment protocol can be formulated for the prevention or treatment of the proteinuric glomerular disorder specific for the at least one subject. In one embodiment, the at least one subject is at risk for development of a primary or secondary or recurrent proteinuric glomerular disorder such as FSGS, Membranous nephropathy, minimal change disease, IgA nephropathy, Membranoproliferative glomerulopathy, diabetic nephropathy, lupus nephritis, myeloma kidney, hypertensive nephrosclerosis, paucimmune glomerulonephritis, preeclampsia, amyloidosis, cryoglobulinemia, thrombotic thrombocytopenic purpura, Hemolytic uremic syndrome, scleroderma kidney, Alport's glomerulopathy, transplant glomerulopathy, or a storage disorder, and the cytoskeletal disruption or rearrangement includes one or more of: cellular blebbing, cellular enlargement, apoptosis, and loss of stress fibers.

Also described herein is an assay for determining if at least one subject who is at risk for a primary or secondary proteinuric glomerular disorder or who has a primary or secondary proteinuric glomerular disorder is at risk for primary or secondary disease development, progression or recurrence of the proteinuric glomerular disorder after kidney transplantation. The assay includes: obtaining a biological sample from the subject; contacting the biological sample with reporter cells having a vector containing a nucleic acid encoding an SMPDL-3b promoter sequence operably linked to a nucleic acid encoding a reporter gene; analyzing expression levels of the reporter gene in the reporter cells; and correlating a change in reporter gene expression relative to a control with an increased risk for primary or secondary disease development or progression or an increased risk for a recurrence of the proteinuric or glomerular disorder after kidney transplantation in the subject. In the assay, the proteinuric glomerular disorder is typically one of: FSGS, Membranous nephropathy, minimal change disease, IgA nephropathy, Membranoproliferative glomerulopathy, diabetic nephropathy, lupus nephritis, myeloma kidney, hypertensive nephrosclerosis, paucimmune glomerulonephritis, preeclampsia, amyloidosis, cryoglobulinemia, thrombotic thrombocytopenic purpura, Hemolytic uremic syndrome, scleroderma kidney, Alport's glomerulopathy, transplant glomerulopathy, and a storage disorder. The reporter gene can be, for example, a nucleic acid encoding luciferase and the reporter cells are transfectable mammalian cells. The assay can further include analyzing normal human podocytes contacted with the biological sample and quantitatively measuring at least one of: oxygen consumption rate, intracellular lipid accumulation, and apoptosis, and correlating a change in the at least one quantitative measurement relative to a control with an increased risk of development, progression or recurrence of the proteinuric glomerular disorder after kidney transplantation in the subject. In another embodiment, the assay includes analyzing the phenotype quantitatively based on a standard curve generated with two dose-dependent chemicals that increase or decrease SMPDL-3b expression or activity. The assay can further include analyzing normal human podocytes contacted with the biological sample for the presence or absence of cytoskeletal disruptions or rearrangements and correlating the presence of cytoskeletal disruptions or rearrangements in the normal podocytes with an increased risk of development, progression, or recurrence of the proteinuric glomerular disorder after kidney transplantation in the subject. In one embodiment, the at least one subject is at risk for the development of a primary or secondary proteinuric glomerular disorder, and the proteinuric glomerular disorder is one of: FSGS, Membranous nephropathy, minimal change disease, IgA nephropathy, Membranoproliferative glomerulopathy, diabetic nephropathy, lupus nephritis, myeloma kidney, hypertensive nephrosclerosis, paucimmune glomerulonephritis, preeclampsia, amyloidosis, cryoglobulinemia, thrombotic thrombocytopenic purpura, Hemolytic uremic syndrome, scleroderma kidney, Alport's glomerulopathy, transplant glomerulopathy, and a storage disorder.

Still further described herein is an assay for predicting a response in a subject to at least one candidate therapeutic agent for prevention or treatment of a particular proteinuric glomerular or renal-related disease. The assay includes the steps of: obtaining a biological sample from the subject having the particular proteinuric glomerular or renal-related disease; contacting a first portion of the biological sample with a first culture of human podocytes in the presence of the at least one candidate therapeutic agent and contacting a second portion of the biological sample with a second culture of podocytes in the absence of the at least one candidate therapeutic agent; examining the first and second cultures of podocytes for the presence or absence of cytoskeletal disruptions or rearrangements; and correlating an increase in cytoskeletal disruptions or rearrangements in the second culture of podocytes relative to the first culture of podocytes with a positive response to the at least one candidate therapeutic agent. The assay typically includes repeating one or more of these steps until at least one candidate therapeutic agent that is effective for at least one of: restoration of actin cytoskeleton, preservation of actin cytoskeleton, restoration of physiological SMPDL-3b expression, and preservation of physiological SMPDL-3b expression is identified for the treatment or prevention of the particular proteinuric glomerular disease. The at least one candidate therapeutic agent is at least one of: a drug approved for treatment of the particular proteinuric glomerular disease, and an off-label drug. Typically, the at least one candidate therapeutic agent is one that modulates activity or expression of at least one of: SMPDL-3b, ASMase, ceramide, S1P, ABCA1, ABCG1, LDL-rec, ACC1, fatty acid synthase, stearoyil-CoA desaturase, HMG-CoA reductase, and SREBP. For example, the at least one candidate therapeutic agent restores physiological SMPDL-3b expression or activity, preserves physiological SMPDL-3b expression or activity, or prevents degradation of SMPDL-3b. One example of a candidate therapeutic agent is rituximab.

An assay for predicting a response in a subject to at least one candidate therapeutic agent for treatment of a particular proteinuric glomerular or renal-related disease is also described herein. The method includes the steps of: obtaining a biological sample from the subject having the particular proteinuric glomerular or renal-related disease; contacting the biological sample with cells including a vector containing a nucleic acid encoding an SMPDL-3b promoter sequence operably linked to a nucleic acid encoding a reporter gene; contacting the mixture of biological sample and reporter cells with at least one candidate therapeutic agent; analyzing reporter gene expression in the reporter cells after contacted with the biological sample and the at least one candidate therapeutic agent; quantifying the reporter gene expression and comparing the reporter gene expression to a control; and correlating a change in the reporter gene expression relative to the control with the subject's response to the at least one candidate therapeutic agent. The at least one candidate therapeutic agent can be one or more of a drug approved for treatment of the particular proteinuric glomerular disease, and an off-label drug. Typically, the at least one candidate therapeutic agent is one that restores physiological SMPDL-3b expression or activity, preserves physiological SMPDL-3b expression or activity, or that prevents degradation of SMPDL-3b.

Yet further described herein is an assay for identifying at least one therapeutic agent for preventing or treating a primary or secondary or recurrent proteinuric glomerular disorder in at least one subject. The assay includes a first step of contacting reporter cells with at least one of: a proteinuric glomerular disease-specific pool of sera from at least one subject having or at risk for the proteinuric glomerular disease, sera from a subject who does not have the proteinuric glomerular disease, and a chemical that either induces or reduces SMPDL-3b expression in at least one multi-well plate. In the assay, the reporter cells generally include a vector containing a nucleic acid encoding an SMPDL-3b promoter sequence operably linked to a nucleic acid encoding a reporter. Another step of the assay is contacting a first portion of the reporter cells with a library of candidate therapeutic agents, wherein at least a second portion of the reporter cells is not contacted with the library of candidate therapeutic agents. Additional steps of the assay are analyzing reporter gene expression in the first and second portions of reporter cells; identifying at least one therapeutic agent from the library of candidate therapeutic agents that prevents modulation of SMPDL-3b expression, restores SMPDL-3b expression to a control level, or preserves SMPDL-3b expression at a control level; and correlating the therapeutic agent's ability to prevent modulation of SMPDL-3b expression, restore SMPDL-3b expression to the control level or preserve SMPDL-3b expression at the control level with an ability to prevent or treat recurrent proteinuric glomerular disease in the at least one subject. In the assay, the primary or secondary or recurrent proteinuric glomerular disorder is typically one of: FSGS, Membranous nephropathy, minimal change disease, IgA nephropathy, Membranoproliferative glomerulopathy, diabetic nephropathy, lupus nephritis, myeloma kidney, hypertensive nephrosclerosis, paucimmune glomerulonephritis, preeclampsia, amyloidosis, cryoglobulinemia, thrombotic thrombocytopenic purpura, Hemolytic uremic syndrome, scleroderma kidney, Alport's glomerulopathy, transplant glomerulopathy, and a storage disorder. The assay can further include the step of: correlating the therapeutic agent's ability to prevent modulation of SMPDL-3b expression, restore SMPDL-3b expression to a control level, or preserve SMPDL-3b expression at a control level with an ability to prevent or reverse cytoskeletal disruptions or rearrangements observed in at least one culture of podocytes cultured in at least one multi-well plate with sera from the at least one subject having the proteinuric glomerular disease, or with a chemical that induces cytoskeletal rearrangements. Examples of a chemical that induces cytoskeletal rearrangements or preserves cytoskeleton structure include cytokalasin D, lipopolysaccharide, puromycin aminonucleoside, protamine sulphate, phalloidin, and latrunculin.

An assay for identifying at least one therapeutic agent for preventing or treating a primary or secondary or recurrent proteinuric glomerular disorder in at least one subject is described herein. The assay includes: culturing human podocytes in the presence of at least one of: a proteinuric glomerular disease-specific pool of sera from at least one subject having the proteinuric glomerular disease, sera from a subject who does not have the proteinuric glomerular disease, and a chemical that induces, prevents or decreases cytoskeletal disruptions or rearrangements in at least one multi-well plate; contacting the cultured podocytes with one or more candidate therapeutic agents from a library of candidate therapeutic agents; examining the cultured podocytes contacted with one or more candidate therapeutic agents from a library of candidate therapeutic agents for cytoskeletal disruptions or rearrangments; and identifying at least one therapeutic agent which prevents or decreases cytoskeletal disruptions or rearrangements. Generally, the primary or secondary or recurrent proteinuric glomerular disorder is one or more of: FSGS, Membranous nephropathy, minimal change disease, IgA nephropathy, Membranoproliferative glomerulopathy, diabetic nephropathy, lupus nephritis, myeloma kidney, hypertensive nephrosclerosis, paucimmune glomerulonephritis, preeclampsia, amyloidosis, cryoglobulinemia, thrombotic thrombocytopenic purpura, Hemolytic uremic syndrome, scleroderma kidney, Alport's glomerulopathy, transplant glomerulopathy, and a storage disorder. The assay can further include examining the podocytes for expression of at least one factor that affects podocyte function, e.g., SMPDL-3b, ASMase, ceramide, S1P, ABCA1, ABCG1, LDL-rec, ACC1, fatty acid synthase, HMG-CoA reductase, and an SERBP.

Yet further described herein is a method of preventing or treating primary or secondary proteinuric glomerular disorder or recurrent proteinuric glomerular disease in a subject. The method includes the steps of: providing a composition including an agent that restores physiological lipid content in podocytes or physiological lipid-related protein content in podocytes, and a pharmaceutically acceptable carrier; and administering the composition to the subject in a therapeutically effective amount for preventing apoptosis of podocytes, preventing disruption of podocyte cytoskeleton, preventing accumulation of cholesterol and/or lipids in podocytes, and preventing or treating primary or secondary proteinuric glomerular disorder or recurrent proteinuric or glomerular disease in the subject. The primary or secondary proteinuric glomerular disorder or recurrent proteinuric glomerular disease can be, e.g., diabetic nephropathy. The agent that restores physiological lipid content in podocytes or physiological lipid-related protein content in podocytes can be one or more of, for example, rituximab, a cyclodextrin derivative, and an agent that modulates SMPDL-3b expression or activity. In the method, the composition can be administered to the subject at one or more of the following time points: prior to kidney transplantation, during kidney transplantation, and subsequent to kidney transplantation.

A method of preventing progression of FSGS or recurrence of FSGS after kidney transplantation, or treating FSGS in a subject having FSGS is described herein. The method includes administering to the subject a composition including a pharmaceutically acceptable carrier and an agent that is capable of at least one of: increasing SMPDL-3b levels in the subject, restoring cytoskeleton rearrangements in the subject, and decreasing or preventing B7-1 expression or activity in the subject. The composition is administered to the subject having FSGS in an amount effective to prevent or treat FSGS in the subject. The agent can be, for example, rituximab or abatacept. In the method, the composition can be administered to the subject at one or more of the following time points: prior to kidney transplantation, during kidney transplantation, and subsequent to kidney transplantation.

A kit for determining if at least one subject who is at risk for a primary or secondary proteinuric glomerular disorder or who has a primary or secondary proteinuric glomerular disorder is at risk for primary or secondary disease development, progression or recurrence of the proteinuric glomerular disorder after kidney transplantation is described herein. The kit includes: a plurality of reporter cells including a vector containing a nucleic acid encoding an SMPDL-3b promoter sequence operably linked to a nucleic acid encoding a reporter gene; at least one control; and instructions for use.

Also described herein is a kit for predicting a response in at least one subject to at least one candidate therapeutic agent for treatment or prevention of a particular proteinuric glomerular disease. The kit includes: a plurality of reporter cells including a vector containing a nucleic acid encoding an SMPDL-3b promoter sequence operably linked to a nucleic acid encoding a reporter gene; a plurality of candidate therapeutic agents; at least one control; and instructions for use.

Additionally described herein is a kit for determining if at least one subject who is at risk for a primary or secondary proteinuric glomerular disorder or who has a primary or secondary proteinuric glomerular disorder is at risk for primary or secondary disease development, progression or recurrence of the proteinuric glomerular disorder after kidney transplantation. The kit includes: at least one container of podocytes; cytochalasin D as a positive control; a dye for actin cytoskeleton; and instructions for use.

Still further described herein is a kit for predicting a response in at least one subject to at least one candidate therapeutic agent for treatment of a particular proteinuric or glomerular disease. The kit includes: at least one container of podocytes; cytochalasin D as a positive control; a dye for actin cytoskeleton; a plurality of candidate therapeutic agents; and instructions for use.

A method of preventing or treating a renal-related disorder in a subject is described herein. The method includes administering to the subject a composition including one or more of: a cyclodextrin, a cyclodextrin derivative, and a cellular cholesterol-lowering agent that is not a statin, in an amount effective for reducing at least one of: plasma membrane cholesterol, plasma membrane lipids, cellular cholesterol, and cellular lipids in the subject. The renal-related disease may be primary glomerulopathy, secondary glomerulopathy, or a post-transplant recurrence of a glomerular disease such as: FSGS, Membranous nephropathy, minimal change disease, IgA nephropathy, Membranoproliferative glomerulopathy, diabetic nephropathy, lupus nephritis, myeloma kidney, hypertensive nephrosclerosis, paucimmune glomerulonephritis, preeclampsia, amyloidosis, cryoglobulinemia, thrombotic thrombocytopenic purpura, Hemolytic uremic syndrome, scleroderma kidney, Alport's glomerulopathy, transplant glomerulopathy storage disorder, stroke, peripheral vascular disease, diabetes, coronary artery disease, congestive heart failure, atherosclerosis, cardiac hypertrophy, myocardial infarction, endothelial dysfunction and hypertension. The composition is administered in an amount effective for preserving podocyte function and preventing or treating proteinuria in the subject. Typically, administration of the composition results in reduction of at least one of: plasma membrane cholesterol, plasma membrane lipids, cellular cholesterol, and cellular lipids in podocytes of the kidney of the subject. The composition can further include one or more of the following drugs: immunosuppressive agent, ACTH agonist, insulin sensitizer, GH antagonist, antinflammatory medication, vitamin D derivative, RAS system inhibitor, aldosterone inhibitor, HMG-CoA reductase inhibitor, cholesterol absorption inhibitor, bile acid sequestrant, bile acid resin, Niacin, Niacin derivative, fibrate, cholesteryl ester transfer protein (CETP) inhibitor, Acetyl-Coenzyme A acetyltransferase (ACAT) inhibitor, and microsomal triglyceride transport inhibitor.

Unless otherwise defined, all technical terms used herein have the same meaning as commonly understood by one of ordinary skill in the art to which this invention belongs.

As used herein, "protein" and "polypeptide" are used synonymously to mean any peptide-linked chain of amino acids, regardless of length or post-translational modification, e.g., glycosylation or phosphorylation.

By the term "gene" is meant a nucleic acid molecule that codes for a particular protein, or in certain cases, a functional or structural RNA molecule.

As used herein, a "nucleic acid" or a "nucleic acid molecule" means a chain of two or more nucleotides such as RNA (ribonucleic acid) and DNA (deoxyribonucleic acid).

As used herein, the terms "kidney disease(s)," "renal disease," "renal disorder," and "kidney disorder(s)" "kidney injury", "renal injury", "proteinuria", "albuminuria" "podocytopathy," "glomerulopathy", "tubulopathy", "tubular disorder", "nephritic syndrome" "nephrotic syndrome" and "nephropathy" are interchangeable and mean any disease, disorder, syndrome, anomaly, pathology, or abnormal condition of the kidney or of the structure or function of its constituent parts.

As used herein, "proteinuria" refers to an amount of protein larger than 150 mg passing through the kidney filtration barrier in a 24 hour period. "Albuminuria" can be defined as the selective passage of albumin through the filtration barrier, and it is defined as "microalbuminuria" when ranging between 30 and 300 mg/g creatinine and "macroalbuminuria" when above 300 mg/g creatinine in a spot urine collection. Albuminuria and proteinuria are often a consequence of damage to the podocyte, a key constituent of the glomerular filtration barrier that normally would not allow for any protein passage. Proteinuria is a characteristic finding in many renal (kidney) diseases and/or glomerulopathy that can either be idiopatic, genetic or secondary to systemic diseases such as hypertension, eclampsia, diabetes mellitus, lupus, vasculitidis, hemathologic disorder, amyloidosis, cancer, allergic reactions, toxic insult by many drug/agents and transplant glomerulopathy among many other less common causes. Many of these diseases can manifest with nephrotic range proteinuria (i.e., proteinuria larger than 3.5 grams per day or larger than 3.5 g/g creatinine) and manifest as nephrotic syndrome when associated with hypoalbuminemia, hyercoagulability, hypercholesterolemia and edema.

By the term "proteinuric glomerular disorder" is any primary, secondary or post-transplant glomerular disorder associated with the loss of albumin and/or protein as defined above in 0018.

The terms "patient," "subject" and "individual" are used interchangeably herein, and mean an animal (e.g., a mammal such as a human, a vertebrate) subject to be treated and/or to obtain a biological sample from.

As used herein, "bind," "binds," or "interacts with" means that one molecule recognizes and adheres to a particular second molecule in a sample or organism, but does not substantially recognize or adhere to other structurally unrelated molecules in the sample. Generally, a first molecule that "specifically binds" a second molecule has a binding affinity greater than about $10^8$ to $10^{12}$ moles/liter for that second molecule and involves precise "hand-in-a-glove" docking interactions that can be covalent and noncovalent (hydrogen bonding, hydrophobic, ionic, and van der waals).

The term "labeled," with regard to a nucleic acid, protein, probe or antibody, is intended to encompass direct labeling of the nucleic acid, protein, probe or antibody by coupling (i.e., physically or chemically linking) a detectable substance (detectable agent) to the nucleic acid, protein, probe or antibody.

When referring to a nucleic acid molecule or polypeptide, the term "native" refers to a naturally-occurring (e.g., a wild type, WT) nucleic acid or polypeptide.

By the term "off label" when referring to a drug or compound means that the drug or compound is used in a different way than described in the FDA-approved drug or compound label.

As used herein, the terms "therapeutic," and "therapeutic agent" are used interchangeably, and are meant to encompass any molecule, chemical entity, composition, drug, therapeutic agent, chemotherapeutic agent, or biological agent capable of preventing, ameliorating, or treating a disease or other medical condition. The term includes small molecule compounds, antisense reagents, siRNA reagents, antibodies, enzymes, peptides organic or inorganic molecules, cells, natural or synthetic compounds and the like.

As used herein, the terms "diagnostic," "diagnose" and "diagnosed" mean identifying the presence or nature of a pathologic condition.

The term "sample" is used herein in its broadest sense. A sample including polynucleotides, peptides, antibodies and the like may include a bodily fluid, a soluble fraction of a cell preparation or media in which cells were grown, genomic DNA, RNA or cDNA, a cell, a tissue, skin, hair and the like. Examples of samples include saliva, serum, tissue, skin, blood, urine and plasma.

As used herein, the term "treatment" is defined as the application or administration of a therapeutic agent to a patient or subject, or application or administration of the therapeutic agent to an isolated tissue or cell line from a patient or subject, who has a disease, a symptom of disease or a predisposition toward a disease, with the purpose to cure, heal, alleviate, relieve, alter, remedy, ameliorate, improve, prevent or affect the disease, the symptoms of disease, or the predisposition toward disease.

Although assays, compositions, kits, and methods similar or equivalent to those described herein can be used in the practice or testing of the present invention, suitable assays, compositions, kits, and methods are described below. All publications, patent applications, and patents mentioned herein are incorporated by reference in their entirety. In the case of conflict, the present specification, including definitions, will control. The particular embodiments discussed below are illustrative only and not intended to be limiting.

BRIEF DESCRIPTION OF THE DRAWINGS

FIG. 1A-FIG. 1E: Shows that both rituximab and SMPDL-3b partially prevent the effect of recurrent FSGS sera on podocyte stress fibers. FIG. 1A: Shows representative stress fiber confocal images of normal human podocytes exposed to normal (NHS) (n=5), non-recurrent (NON-REC) FSGS (n=10), and recurrent (REC) FSGS (n=12) human sera. Scale bars, 10 μm. FIG. 1B: Depicts the percentage of cells with disruption of stress fibers observed after exposure to NHS (n=5), non-recurrent sera (n=10), and recurrent human sera (n=12). ***p<0.001 by one-way ANOVA. FIG. 1C: Depicts the linear correlation between the percentage of cells with loss of stress fibers and the urine protein/creatinine ratio obtained from REC and NON-REC patients (n=22) in the first 30 days after transplantation ($R^2$=0.59; p<0.001 calculated with an F test with 18 degrees of freedom). FIG. 1D: Depicts confocal images of stress fibers and corresponding bar graph analysis of normal human podocytes exposed to recurrent FSGS sera in the presence (REC+RITUX) or absence (REC) of rituximab. Rituximab protected the loss of stress fibers observed in stressed podocytes exposed to recurrent FSGS, but not non-recurrent FSGS human sera. Scale bars, 10 μm, data are mean±s.d. *p<0.05; ***p<0.001 by one-way ANOVA. FIG. 1E: Depicts confocal images of stress fibers and corresponding bar graph analysis of normal human podocytes exposed to REC sera transfected with an empty GFP vector (REC) or with a SMPDL-3b-GFP vector (REC+SMPDL-3b). SMPDL-3b overexpression protected the loss of stress fibers observed in podocytes exposed to recurrent FSGS human sera, data are mean±s.d. *p<0.05; ***p<0.001 by one-way ANOVA. The in vitro studies strongly correlate to in vivo clinical outcome data, as rituximab administered in patients at high risk for recurrent FSGS after transplantation significantly protected from the development of post transplant proteinuria as demonstrated in Table 1.

FIG. 2A: Depicts low- and high-power images of immunoperoxidase staining for SMPDL-3b and synaptopodin in post-reperfusion biopsies of patients with recurrent (REC) and non-recurrent (NON-REC) FSGS. Arrows point to podocytes. Scale bars: 25 μm top and 15 μm bottom. FIG. 2B: Depicts the number of SMPDL-3b+ podocytes per glomerulus, as evaluated by SMPDL-3b and synaptopodin labeling in post-reperfusion kidney biopsies from patients that later on developed recurrent (REC) disease (n=8) and patients that did not develop clinical recurrence (NON-REC) (n=12). All kidney biopsies were obtained prior to initiation of treatment with rituximab. An average of 13±4 glomeruli per patient were analyzed. *p<0.05, unpaired Student's t test. Data are mean±s.d. FIG. 2C: Shows regulation of podocyte SMPDL-3b mRNA expression by normal (NHS), non-recurrent (NON-REC) FSGS, and recurrent (REC) FSGS human sera (n=4 per group) and by rituximab. Data are mean±s.d. *p<0.05 and **p<0.01 by one-way ANOVA. FIG. 2D: Depicts the amount of SMPDL-3b protein is normalized to actin in human podocytes treated with normal (n=5), recurrent (n=12), or non-recurrent (n=10) human sera and exposed to rituximab. Data are mean±s.d. *p<0.05 and **p<0.01 by one-way ANOVA. FIG. 2E: Shows western blot for SMPDL-3b protein of normal podocytes cultured with sera from consecutive non-recurrent (n=4) and recurrent (n=4) FSGS patients in the presence or absence of rituximab. FIG. 2F: Depicts the amount of 52 and 54 kDa ASMase protein is normalized to actin in human podocytes that were exposed to normal (n=5), non-recurrent FSGS (n=10), and recurrent FSGS (n=12) human sera in the presence or absence of rituximab. Data are mean±s.d. *p<0.05 and **p<0.01 by one-way ANOVA. FIG. 2G: Shows ASMase activity per μg of total lysate protein, as evaluated by ELISA. Data are mean±s.d. *p<0.05 and **p<0.01 by one-way ANOVA.

FIG. 3A-FIG. 3F: Shows regulation of actin stress fibers and cholesterol content in human podocytes exposed to the sera of patients with DM with or without DN. FIG. 3A: Shows confocal stress fiber images and bright field images of podocytes exposed to the three different groups of sera demonstrating cell blebbing. FIG. 3B: Shows quantification of cells with blebs in cells exposed to DM w DN sera when compared to cells exposed DM w/o DN sera or NHS. FIG. 3C: Depicts representative immunofluorescence images for cholesterol content (filipin staining), and phosphorylated caveolin and DAPI in podocytes exposed to the three different groups of sera demonstrating that DM w DN sera causes lipid accumulation and peripheral distribution of p-caveolin, a phenomenon that can be prevented by CD. FIG. 3D: Shows quantitative bar graph analysis of total cholesterol in podocytes exposed to DM w DN sera when compared to DM w/o DN and NHS. Total cholesterol (TC) significantly increased in podocytes exposed to DM w DN sera, a phenomenon that could be prevented by CD. FIG. 3E: Shows confocal images of cell blebbing observed after exposure to the sera of diabetic patients before and after progressing to DN, demonstrating that cell blebbing precedes DN. FIG. 3F: Depicts quantitative bar graph analysis of cleaved caspase 3 in podocytes exposed to DM w DN sera when compared to DM w/o DN and NHS showing increased apoptosis in podocytes exposed to DM w DN sera, a phenomenon that could be prevented by CD.

FIG. 4A: Shows double labeling confocal microscopy with the podocyte protein synaptopodin shows podocyte B7-1 expression in post- but not pre-transplant biopsy in recurrent FSGS. Podocyte B7-1 expression was seen in 3 out of 5 glomeruli in the depicted post-transplant FSGS case. FIG. 4B: Shows detection of podocyte FP effacement in the post- but not pre-transplant biopsy. FIG. 4C: Depicts serum levels of creatinine (filled circle) and urinary protein/creatinine ratios in post-transplant (empty triangle) after Abatacept and plasmapheresis (PP) treatment. Concomitant serum albumin levels are given in mg/dl (filled square).

FIG. 5A: Shows human podocytes deficient of SMPDL-3b (siSMP) are characterized by increased cholesterol content when compared to control podocytes (CTRL). FIG. 5B: Shows that siSMP podocytes are characterized by decreased ASMase activity when compared to CTRL (***$p<0.001$).

FIG. 6A: Depicts the results when HPBCD was administered intravenously (4000 mg/kg) 1 hour prior to LPS injection (200 ug/20 g mouse intraperitoneally). Urines were collected 48 hours after LPS injection and analyzed for albumin/creatinine ratio by ELISA. $p<0.05$ when comparing LPS+CD versus LPS. FIG. 6B: Depicts that CD prevented LPS induction of MyD88 in isolated glomeruli in vivo.

DETAILED DESCRIPTION

Figure 2A:
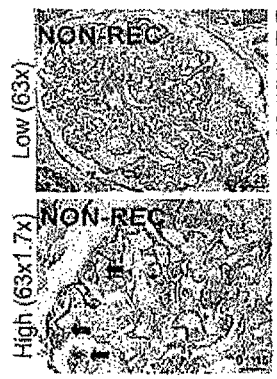
FIG. 2A-FIG. 2G: Shows that rituximab prevents the downregulation of SMPDL-3b in recurrent FSGS.
Figure 2B:
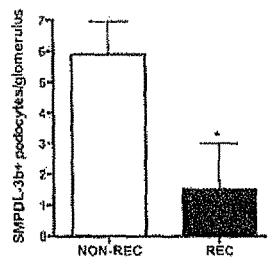
Figure 2C:
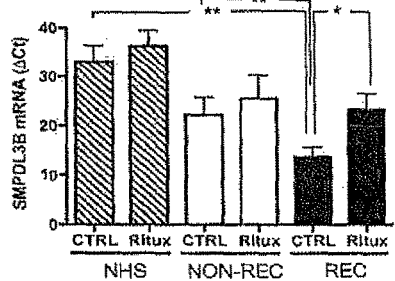
Figure 2D:
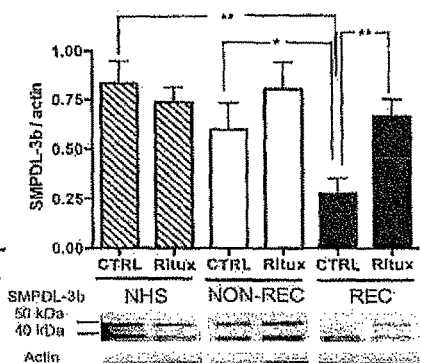
Figure 2E:
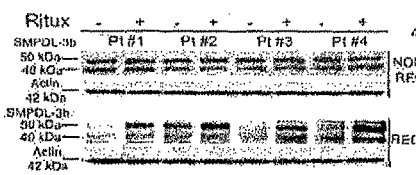
Figure 2E:
Figure 2G:
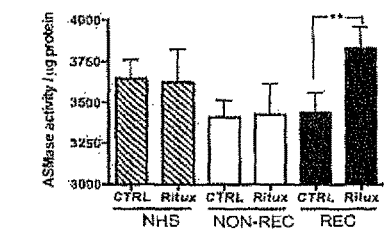
Figure 2F:
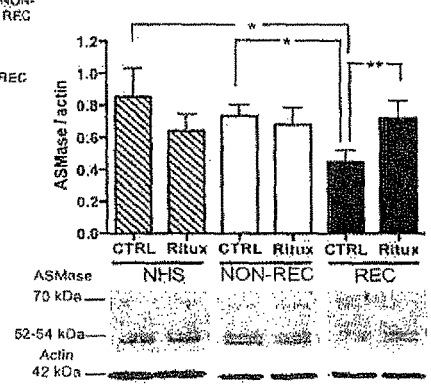

Described herein are assays, methods and kits for predicting a subject's (e.g., human) risk of development or progression of a glomerular disease (e.g., FSGS, DN, Membranous nephropathy, minimal change disease, IgA nephropathy, Membranoproliferative glomerulopathy, lupus nephritis, myeloma kidney, hypertensive nephrosclerosis, paucimmune glomerulonephritis, preeclampsia, amyloidosis, cryoglobulinemia, thrombotic thrombocytopenic purpura, Hemolytic uremic syndrome, scleroderma kidney, Alport's glomerulopathy, storage disorders and other rate genetic disorders). Described herein are assays for predicting, for example, if a diabetic subject will develop glomerular or kidney disease, assays for identifying a new or previously available therapeutic agent for preventing or treating a glomerular disease, and assays for establishing a personalized approach to treat or prevent a glomerular disease in a subject. A high-throughput platform will find particular use for the development of therapeutics to treat renal diseases such as FSGS. Based on the experimental results described below, serum-induced cytoskeletal disruptions and rearrangements, as well as modulation of SMPDL-3b expression, stability or activity, as well as lipid content, oxygen consumption rate, and apoptosis in normal, healthy human podocytes may be used as a marker for predicting recurrent glomerular disease (e.g., recurrent FSGS) in a pre-transplant patient. The assays, methods and kits may be used for any glomerular disease (e.g., FSGS, DN, Membranous nephropathy, minimal change disease, IgA nephropathy, Membranoproliferative glomerulopathy, lupus nephritis, myeloma kidney, hypertensive nephrosclerosis, paucimmune glomerulonephritis, preeclampsia, amyloidosis, cryoglobulinemia, thrombotic thrombocytopenic purpura, Hemolytic uremic syndrome, scleroderma kidney, Alport's glomerulopathy, storage disorders and other rate genetic disorders), providing the ability to predict the clinical course of a disease and to develop personalized treatment strategies. This new technology may be used as an easily performed assay for use worldwide as a prognostic tool for primary, secondary or transplant related glomerular diseases and as a predictive tool for the identification of disease-specific prevention and treatment strategies. Further described herein are compositions, kits and methods for treating glomerular and kidney diseases.

Biological and Chemical Methods

Methods involving conventional molecular biology techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., 2001; and Current Protocols in Molecular Biology, ed. Ausubel et al., Greene Publishing and Wiley-Interscience, New York, 1992 (with periodic updates). Conventional methods of culturing mammalian cells, e.g., human podocytes, are generally known in the art. Methods of culturing podocytes are described in detail in Saleem M A, O'Hare M J, Reiser J, et al., J Am Soc Nephrol 2002; 13(3):630-8. Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233. The amino acid sequence of SMPDL-3b and the nucleic acid sequence encoding SMPDL-3b are known as accession numbers NM_001009568.1 and NM_014474.2. For a reference describing the characterization of SMPDL-3b, see, for example, Perosa et al., Blood vol. 107:1070-1077, 2006.

Assays for Predicting Responses to Treatment in a Subject

Described herein are assays for predicting a response in a subject to at least one candidate therapeutic agent for treatment of a particular proteinuric glomerular or renal-related disease. In one embodiment, the assay includes: obtaining a biological sample from the subject at risk for or having the particular proteinuric glomerular or renal-related disease; contacting a first portion of the biological sample with a first culture of human podocytes in the presence of the at least one candidate therapeutic agent and contacting a second portion of the biological sample with a second culture of podocytes in the absence of the at least one candidate therapeutic agent; examining the first and second cultures of podocytes for the presence or absence of cytoskeletal disruptions or rearrangements; and correlating an increase in cytoskeletal disruptions or rearrangements in the second culture of podocytes relative to the first culture of podocytes with a positive response to the at least one candidate therapeutic agent. In this assay, one or more of these steps can be repeated until at least one candidate therapeutic agent that is effective for restoration of actin cytoskeleton and/or physiological SMPDL-3b expression and for the treatment of the particular proteinuric glomerular disease is identified.

In another embodiment, the assay includes: obtaining a biological sample from the subject having the particular proteinuric glomerular or renal-related disease; contacting the biological sample with cells comprising a vector containing a nucleic acid encoding the SMPDL-3b promoter sequence operably linked to a nucleic acid encoding a reporter gene; contacting the mixture of biological sample and reporter cells with at least one candidate therapeutic agent; analyzing reporter gene expression in the reporter cells after contacted with the biological sample and the at least one candidate therapeutic agent; quantifying the reporter gene expression and comparing the reporter gene expression to a control; and correlating a change in the reporter gene expression relative to the control with the subject's response to the at least one candidate therapeutic agent.

In these embodiments, the at least one candidate therapeutic agent can be one or more of a drug approved for treatment of the particular proteinuric glomerular disease, and/or an off-label drug. In a typical embodiment, the at least one candidate therapeutic agent is one that restores physiological SMPDL-3b expression or activity, or that prevents degradation of SMPDL-3b (e.g., rituximab). Additionally or alternatively, the at least one candidate therapeutic agent can be one that modulates activity or expression of, for example, ASMase, ceramide, SIP, ABCA1, ABCG1, LDL-rec, ACC1, fatty acid synthase, stearoyil-CoA desaturase, HMG-CoA reductase, and SREBP.

In one embodiment, the assay includes examining the podocytes for the presence or absence of cytoskeletal disruptions or rearrangements, lipid accumulation, modulation of SMPDL-3b, and/or apoptosis, resulting in determination of a first phenotype of the podocytes. This first phenotype can be compared with one or more controls. For example, the first phenotype can be compared with a second phenotype of podocytes contacted with a biological sample from at least one normal subject, and a third phenotype of podocytes contacted with a biological sample from at least one subject with the glomerular disorder (e.g., recurrent FSGS). In such an embodiment, the second phenotype is typically a negative control, and the third phenotype a positive control. Such an assay can be used to determine a patient-specific response to one or more therapeutic strategies that have been approved for the treatment of the medical condition being treated in the patient, as well as therapies that may be utilized off label. As an example, for any given patient with diabetes, the in vitro response to established treatment strategies (such as ACE inhibitors, Angiotensin receptor blockers, aldosterone antagonists, vitamin D analogues, etc.) will be tested in conjunction with off label treatment strategies (e.g., cyclodextrin derivatives, abatacept, rituximab, belimumab, atacicept, alefacept, etc.). Using such an assay, off label treatment strategies that are effective in vitro may be tested in vivo, and may therefore allow for the identification of optimal personalized treatment strategies for any patient with any renal disorder.

Assay for Determining Risk for Primary or Secondary Proteinuric Glomerular Disorder Development, Progression or Recurrence after Kidney Transplantation Assays for determining if at least one subject (e.g., 1, 2, 3, 4, 5, 10, 50, 100, etc.) who is at risk for or has a primary or secondary proteinuric glomerular disorder is at risk for primary or secondary disorder progression or is at risk for a recurrence of the proteinuric glomerular disorder after kidney transplantation. In one embodiment, the assay includes contacting a biological sample from the at least one subject with a culture of human podocytes; examining the podocytes for the presence or absence of cytoskeletal disruptions or rearrangements resulting in determination of a first phenotype of the podocytes; and correlating the presence of cytoskeletal disruptions or rearrangements with an increased risk of development, recurrence, or progression of the proteinuric glomerular disorder (e.g., FSGS, DN, Membranous nephropathy, minimal change disease, IgA nephropathy, Membranoproliferative glomerulopathy, lupus nephritis, myeloma kidney, hypertensive nephrosclerosis, paucimmune glomerulonephritis, preeclampsia, amyloidosis, cryoglobulinemia, thrombotic thrombocytopenic purpura, Hemolytic uremic syndrome, scleroderma kidney, Alport's glomerulopathy, storage disorders and other rate genetic disorders) in the subject. Any biological sample can be used, e.g., blood, saliva, serum, plasma, tissue, and urine. The assay may be used for one subject, or a plurality of subjects who have a primary, secondary or post-transplant proteinuric glomerular disorder. The cytoskeletal disruptions or rearrangements can be examined by any suitable method, e.g., microscopy, Western blotting, ELISA, flow cytometry, reporter gene assays. Generally, the first phenotype is compared to a negative control and a positive control. The assay can further include analyzing the first phenotype quantitatively based on a standard curve generated with a dose-dependent chemical disruption of actin cytoskeleton.

In another embodiment of an assay for determining if at least one subject (e.g., 1, 2, 3, 4, 5, 10, 50, 100, etc.) who has or is at risk for a primary or secondary proteinuric glomerular disorder is at risk for primary or secondary disease progression or is at risk for a recurrence of the proteinuric glomerular disorder after kidney transplantation, the assay includes the steps of: obtaining a biological sample from the subject; contacting the biological sample with reporter cells (e.g., transfectable mammalian cells) including a vector containing a nucleic acid encoding the SMPDL-3b promoter sequence operably linked to a nucleic acid encoding a reporter gene (e.g., a nucleic acid encoding luciferase); analyzing expression levels of the reporter gene in the reporter cells; and correlating a change in reporter gene expression relative to a control with an increased risk for primary or secondary disease development and/or progression or an increased risk for a recurrence of the proteinuric or glomerular disorder. In this embodiment, the assay can further include analyzing normal human podocytes contacted with the biological sample and quantitatively measuring at least one of: oxygen consumption rate, intracellular lipid accumulation, and apoptosis, and correlating a change in the at least one quantitative measurement relative to a control with an increased risk of development, progression or recurrence of the primary or secondary proteinuric glomerular disorder in the subject. The first phenotype can be quantitatively based on a standard curve generated with two dose-dependent chemicals that increase or decrease SMPDL-3b expression or activity. The assay can further include the step of analyzing normal human podocytes contacted with the biological sample for the presence or absence of cytoskeletal disruptions or rearrangements and correlating the presence of cytoskeletal disruptions or rearrangements with an increased risk of development, recurrence, or progression of the proteinuric glomerular disorder in the subject.

In some embodiments, the at least one subject is identified as having an increased risk for development of primary, secondary or recurrent proteinuric glomerular disease, and a personalized treatment protocol is formulated for the prevention or treatment of the proteinuric glomerular disorder specific for the at least one subject. The at least one subject may be at risk for development of a primary or secondary proteinuric glomerular disorder such as, for example, FSGS, Membranous nephropathy, minimal change disease, IgA nephropathy, Membranoproliferative glomerulopathy, diabetic nephropathy, lupus nephritis, myeloma kidney, hypertensive nephrosclerosis, paucimmune glomerulonephritis, preeclampsia, amyloidosis, cryoglobulinemia, thrombotic thrombocytopenic purpura, Hemolytic uremic syndrome, scleroderma kidney, Alport's glomerulopathy, transplant glomerulopathy, and a storage disorder, and the cytoskeletal disruption or rearrangement includes at least one of: cellular blebbing, cellular enlargement, apoptosis, and loss of stress fibers.

The assays and methods described herein can be used for determining if a subject (e.g., human) who is considering receiving or is planning to receive a kidney transplant is at risk for recurrent FSGS after kidney transplantation. One example of such an assay includes the following steps: contacting a biological sample from at least one subject who has FSGS with a culture of normal human podocytes; examining the podocytes for the presence or absence of cytoskeletal disruptions or rearrangements resulting in determination of a first phenotype of the podocytes; and correlating the presence of cytoskeletal disruptions or rearrangements with an increased risk of FSGS recurring in at least one subject subsequent to a kidney transplantation compared to subjects without recurrent FSGS or to subjects being transplanted for FSGS unrelated causes. Actin cytoskeleton remodeling can be utilized alone or in combination with the modulation of SMPDL-3b expression, lipid content, oxygen consumption rate, apoptosis. The biological sample is obtained prior to the kidney transplantation and initiation of immunosuppression in the subject so that the subject's risk of having recurrent FSGS post-transplant can be assessed. In the experiments described herein, sera from subjects were used. In some embodiments, biological samples from a plurality of subjects suspected of having or being at risk of developing FSGS can be analyzed simultaneously, e.g., in a high-throughput format. Any suitable biological sample can be contacted with the cultured podocytes. Examples of biological samples include blood, saliva, serum, plasma, tissue, and urine.

Typically, the subject is suspected of developing or is at high risk of developing FSGS after receiving a kidney transplant when certain risk factors are present, primarily age of the patient (less than 15 years of age) and time from diagnosis to ESRD (less than 3 years). The assay includes appropriate positive and negative controls. For example, the assay can include comparing the first phenotype with a second phenotype of podocytes contacted with a biological sample from at least one normal subject as a negative control, and a third phenotype of podocytes contacted with a biological sample from at least one subject with recurrent FSGS as a positive control. Because of the limited availability of biological samples to be utilized as standardized positive controls, a stable chemical agent can be utilized at different concentrations to disrupt the actin cytoskeleton (Cytochalasin D). Such an approach will allow for the development of a dose-dependent standard curve that will facilitate the standardized quantification of stress fiber disruption when human podocytes will be exposed to patient sera In some embodiments, at least one subject includes a plurality (e.g., 2, 3, 4, 5, 10, 15, 20, 25, 30, 35, 40, 50, 100, etc.) of subjects who have FSGS. In the experiments described below, disruption of podocyte stress fibers was examined. However, other podocyte abnormalities or disturbances in cultured podocyte functions can be examined in an assay or method, such as the disruption of podocyte specific proteins involved in actin cytoskeleton remodeling (synaptopodin) or the translocation of relevant plasma membrane proteins (nephrin, podocin, CD2AP) from the plasma membrane (physiologic) to the cytosol (pathologic), the accumulation of podocyte cellular lipids (e.g. sterols, sphingolipids, triglycerides, free fatty acids, glycosphingolipids, ceramides) and/or the expression of any factor capable of altering the expression of SMPDL-3b or any other lipid related protein (e.g. ASMase, S1P, ABCA1, ABCG1, LDL-rec, ACC1, fatty acid synthase, stearoyil-CoA desaturase, HMG-CoA reductase, SERBPs) in podocytes.

One or more methods can be used in the detection of podocyte abnormalities. In one aspect, podocyte abnormalities can be detected using, for example, microscopy (e.g., electron microscopy, light microscopy, fluorescence microscopy). Using microscopy or other suitable means for examining podocytes, the step of examining the podocytes for the presence or absence of cytoskeletal disruptions or rearrangements results in determination of a first phenotype of the podocytes and includes counting the number of podocytes that display cyto skeletal disruptions or rearrangements. Generally, the assay includes analyzing a standard curve built with different doses of a stable chemical or biological positive control.

Any non-primary culture of normal human podocytes can be used in the assays, methods and kits described herein. The podocytes can be cultured under any appropriate culture conditions. In the experiments described herein, the normal human podocytes were cultured according to Saleem M A, O'Hare M J, Reiser J, et al., J Am Soc Nephrol 2002; 13(3):630-8. This immortalized human podocyte cell line allows for the generation of a sufficient number of podocytes when cultured in permissive conditions at 33° C. Cells will then achieve terminal differentiation and will growth arrest with development of the classical octopus morphology once thermoshifted at 37° C. for 14 days.

As described above for an assay for predicting a response to treatment in a subject having a glomerular disorder, an assay for determining if a subject (e.g., human) who is at risk for occurrence or recurrence of a glomerular or proteinuric disorder (e.g., FSGS, DN, Membranous nephropathy, minimal change disease, IgA nephropathy, Membranoproliferative glomerulopathy, lupus nephritis, myeloma kidney, hypertensive nephrosclerosis, paucimmune glomerulonephritis, preeclampsia, amyloidosis, cryoglobulinemia, thrombotic thrombocytopenic purpura, Hemolytic uremic syndrome, scleroderma kidney, Alport's glomerulopathy, storage disorders and other rate genetic disorders) can include examining modulation of SMPDL-3b in cells (e.g., podocytes). An example of such an assay includes: contacting a biological sample from the at least one subject with a culture of human podocytes; examining the podocytes for modulation of SMPDL-3b resulting in determination of a first phenotype of the podocytes; and correlating the modulation of SMPDL-3b with an increased risk of occurrence or recurrence of a glomerular or proteinuric disorder (e.g., FSGS, DN, Membranous nephropathy, minimal change disease, IgA nephropathy, Membranoproliferative glomerulopathy, lupus nephritis, myeloma kidney, hypertensive nephrosclerosis, paucimmune glomerulonephritis, preeclampsia, amyloidosis, cryoglobulinemia, thrombotic thrombocytopenic purpura, Hemolytic uremic syndrome, scleroderma kidney, Alport's glomerulopathy, storage disorders and other rate genetic disorders) The assay can further include comparing the first phenotype with a second phenotype of podocytes contacted with a biological sample from at least one normal subject, and a third phenotype of podocytes contacted with a biological sample from at least one subject with the proteinuric or glomerular disorder (e.g., FSGS, DN, Membranous nephropathy, minimal change disease, IgA nephropathy, Membranoproliferative glomerulopathy, lupus nephritis, myeloma kidney, hypertensive nephrosclerosis, paucimmune glomerulonephritis, preeclampsia, amyloidosis, cryoglobulinemia, thrombotic thrombocytopenic purpura, Hemolytic uremic syndrome, scleroderma kidney, Alport's glomerulopathy, storage disorders and other rate genetic disorders). The second phenotype is typically a negative control, and the third phenotype a positive control. In the assay, modulation of SMPDL-3b can be analyzed by Western blotting, PCR or any SMPDL-3b reporter activity. For the latter, any assay kit in which the SMPDL3b promoter has been cloned into a vector that contains a firefly luciferase gene and a eukaryotic selection marker cassette but that lacks eukaryotic promoter and enhancer sequences is suitable. Thus, luciferase activity observed in cells transfected with such construct will correlate with the expression of the SMPDL3b gene in any culture system. The SMPDL3b-promoter-Luciferase construct could be used to generate stable transfected human podocytes, HEK cell lines or other mammalian cell lines. Cell lines will be used to quantify SMPDL3b promoter-activity and SMPDL3b expression after treatment with the serum of patients being screened.

This assay can further include comparing the first phenotype with a second phenotype of podocytes contacted with a biological sample from at least one normal subject, and a third phenotype of podocytes contacted with a biological sample from at least one subject with the proteinuric or glomerular disorder (e.g., FSGS, DN, Membranous nephropathy, minimal change disease, IgA nephropathy, Membranoproliferative glomerulopathy, lupus nephritis, myeloma kidney, hypertensive nephrosclerosis, paucimmune glomerulonephritis, preeclampsia, amyloidosis, cryoglobulinemia, thrombotic thrombocytopenic purpura, Hemolytic uremic syndrome, scleroderma kidney, Alport's glomerulopathy, storage disorders and other rate genetic disorders). The second phenotype is typically a negative control, and the third phenotype a positive control. Such an assay can be used to predict clinical development of disease and to determine a patient-specific response to one or more therapeutic strategies that have been approved for the treatment of the medical condition being treated in the patient, as well as therapies that may be utilized off label.

Screening Platform for Therapeutics for Proteinuric and Glomerular Diseases

Assays for identifying at least one therapeutic agent for preventing or treating recurrent proteinuric glomerular disease in at least one subject (e.g., a plurality of subjects) are described herein. One assay for identifying at least one therapeutic agent for preventing or treating recurrent proteinuric glomerular disease in at least one subject includes first contacting reporter cells with at least one of: a proteinuric glomerular disease-specific pool of sera from at least one subject having the proteinuric glomerular disease, sera from a subject who does not have the proteinuric glomerular disease, and a chemical that either induces or reduces SMPDL-3b expression in at least one multi-well plate. The reporter cells typically include a vector having a nucleic acid encoding SMPDL-3b operably linked to a nucleic acid encoding a reporter (e.g., luciferase, GFP, etc.). The first portion of the reporter cells are subsequently or concomitantly contacted with (combined with, mixed with) a library of candidate therapeutic agents, while at least a second portion of the reporter cells is not contacted with the library of candidate therapeutic agents. Reporter gene expression is analyzed in the first and second portions of reporter cells. By comparing reporter gene expression in the at least first portion of reporter cells with reporter gene expression in the at least second portion of cells, at least one therapeutic agent (e.g., 1, 2, 3, 4, 5, 10, 50, etc.) from the library of candidate therapeutic agents is identified that prevents modulation of SMPDL-3b expression and/or restores SMPDL-3b expression to a control level. The therapeutic agent's ability to prevent modulation of SMPDL-3b expression or restore SMPDL-3b expression relative to the control level is correlated with an ability to prevent or treat recurrent proteinuric glomerular disease in the at least one subject. Any suitable controls can be used for comparisons. By 'control level' is typically meant podocyte specific physiological SMPDL-3b expression. Such an assay can further include examining at least one culture of podocytes (e.g., normal human podocytes) in which cytoskeletal rearrangements and/or disruptions have been induced by sera from a subject having the proteinuric glomerular disease, or a chemical that induces cytoskeletal rearrangements. For example, the assay can further include correlating the therapeutic agent's ability to prevent modulation of SMPDL-3b expression or restore SMPDL-3b expression to the control level with an ability to prevent or reverse cytoskeletal disruptions or rearrangements observed in at least one culture of podocytes cultured in at least one multi-well plate with sera from at least one subject having the proteinuric glomerular disease, or a chemical that induces cytoskeletal rearrangements (e.g., cytokalasin D, protamine sulphate, lipopolysaccharide, puromycin aminonucleoside, phalloidin, and latrunculin). The podocytes can be analyzed for expression of one or more factors that affect podocyte function, e.g., SMPDL-3b, ASMase, ceramide, S1P, ABCA1, ABCG1, LDL-rec, ACC1, fatty acid synthase, HMG-CoA reductase, and an SERBP.

Another assay for identifying at least one therapeutic agent for preventing or treating recurrent proteinuric or glomerular disease in at least one subject includes first culturing human podocytes in the presence of at least one of: a proteinuric glomerular disease-specific pool of sera from at least one subject having the proteinuric glomerular disease, sera from a subject who does not have the proteinuric glomerular disease, and a chemical that either induces or reduces SMPDL-3b expression in at least one multi-well plate. The cultured podocytes are subsequently or concomitantly contacted with one or more candidate therapeutic agents from a library of candidate therapeutic agents. Next, the cultured podocytes contacted with one or more candidate therapeutic agents from a library of candidate therapeutic agents are examined for cytoskeletal disruptions or rearrangements. By examining the cultured podocytes for a decrease (relative to one or more controls) in cytoskeletal disruptions or rearrangements after exposure to a candidate therapeutic agent, at least one therapeutic agent which prevents or decreases cytoskeletal disruptions or rearrangements can be identified.

Figure 4A:
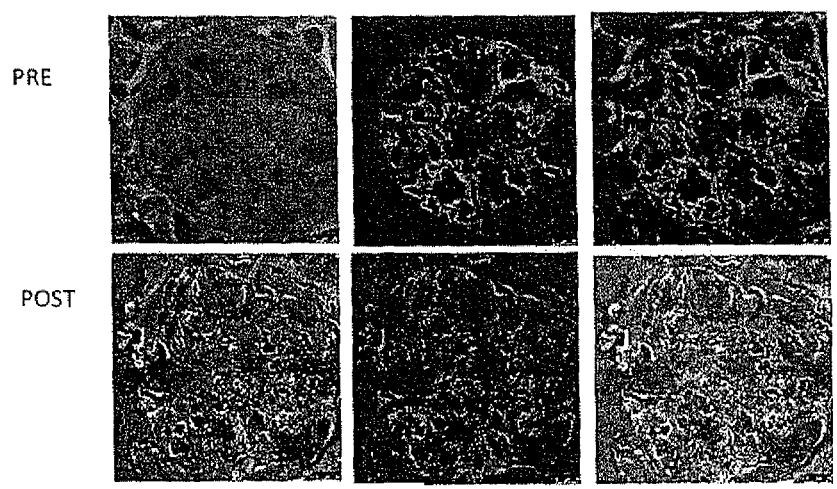
FIG. 4A-FIG. 4C: Shows treatment of proteinuria with Abatacept in patients with recurrent FSGS and biopsy-proven B7-1 podocyte expression.
Figure 4B:
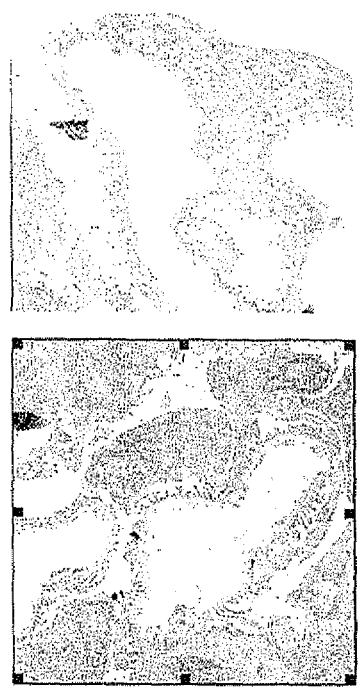
Figure 4C:
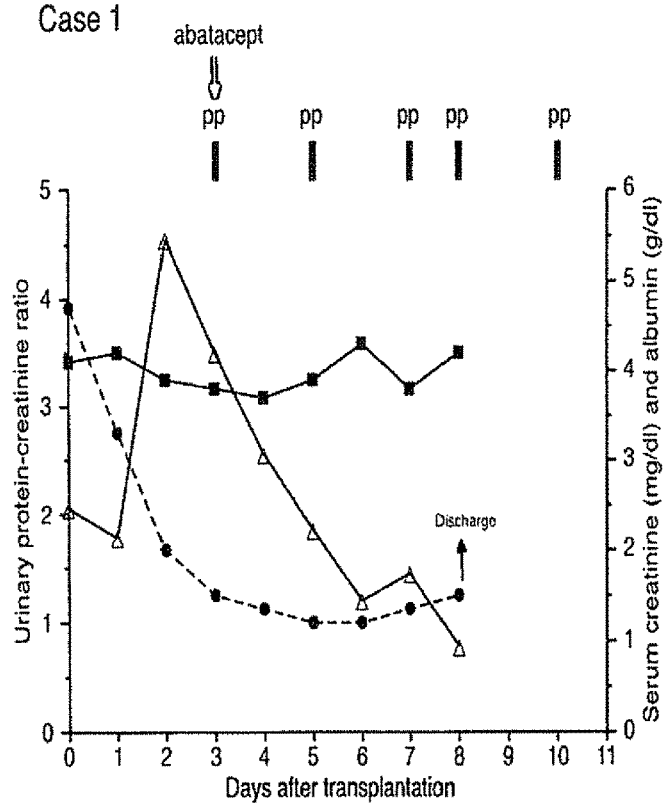
Figure 4C:
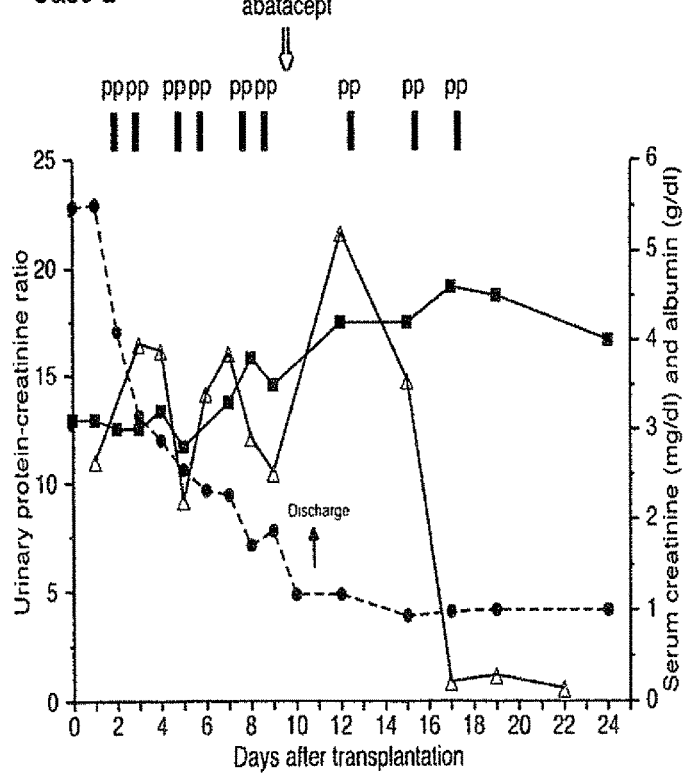

Methods and platforms for screening molecules, compounds, etc., for proteinuric and glomerular disease (e.g., FSGS) therapeutics can include, for example, small molecule screening and other compound screening through any Drug Discovery Core Facility. One example of a method of identifying a therapeutic agent for preventing or treating recurrent proteinuric and glomerular disease (e.g., FSGS) in at least one subject includes the steps of: culturing human podocytes in the presence of a biological sample from at least one subject with high risk for recurrent proteinuric and glomerular disease (e.g., FSGS) (as determined as described above, i.e., the subject is suspected of developing or is at high risk of developing proteinuric and glomerular disease (e.g., FSGS) after receiving a kidney transplant when certain risk factors are present, primarily age of the patient (less than 15 years of age) and time from diagnosis to ESRD (less than 3 years)); contacting the podocytes with one or more candidate therapeutic agents; examining the podocytes for cytoskeletal disruptions; and identifying agents which prevent or decrease cytoskeletal disruptions. Examples of cytoskeletal disruptions include disruption of stress fibers, or any of the read outs for specific podocyte proteins as described above (e.g., the disruption of podocyte specific proteins involved in actin cytoskeleton remodeling (synaptopodin) or the translocation of relevant plasma membrane proteins (nephrin, podocin, CD2AP) from the plasma membrane (physiologic) to the cytosol (pathologic)). Agents that stabilize podocyte cell membranes and prevent their degradation can be used to inhibit podocyte cytoskeletal disruptions in a human. An example of such an agent is one that modulates the activity and/or expression of SMPDL-3b (sphingomyelin-phosphodiesterase-acid-like-3b), such as Rituximab (Perosa F, Favoino E, Caragnano M A, Dammacco F., Blood 2006; 107(3):1070-7). Another example of a drug that may be used to inhibit podocyte cytoskeletal disruptions is abatacept (Orencia®, Bristol-Myers Squibb). In the examples below, clinical tests are described in which abatacept reversed early post-transplant recurrent proteinuria in at least one patient with previous recurrent FSGS (FIGS. 4A-4C).

In one embodiment, a method of identifying a therapeutic agent for preventing or treating recurrent FSGS, DN or any other proteinuric glomerular disorder (FSGS, DN, Membranous nephropathy, minimal change disease, IgA nephropathy, Membranoproliferative glomerulopathy, lupus nephritis, myeloma kidney, hypertensive nephrosclerosis, paucimmune glomerulonephritis, preeclampsia, amyloidosis, cryoglobulinemia, thrombotic thrombocytopenic purpura, Hemolytic uremic syndrome, scleroderma kidney, Alport's glomerulopathy, storage disorders and other rate genetic disorders) includes: culturing human podocytes in the presence of a biological sample from at least one subject with the disease; contacting the podocytes with one or more candidate therapeutic agents; examining the podocytes for cytoskeletal disruptions, excessive or defective SMPDL-3b expression, lipid content, oxygen consumption rate, apoptosis; and identifying agents which prevent or decrease cytoskeletal disruptions, maintain a physiological SMPDL-3b expression, reduce lipid content, reduce oxygen consumption rate, and reduces apoptosis. In the assay, modulation of SMPDL-3b can be analyzed by any suitable methods, e.g., Western blotting, PCR, a SMP luciferase reporter activity assay, etc. Lipid content can be measured by specific enzymatic reactions and by mass spectroscopy, oxygen consumption rate by seahorse technology and apoptosis by ELISA or flow cytometry. The steps of contacting the podocytes with one or more candidate therapeutic agents, examining the podocytes for cytoskeletal disruptions, SMPDL-3b expression, lipid content, oxygen consumption rate, apoptosis; and identifying agents which prevent or decrease cytoskeletal disruptions, restores physiological SMPDL-3b expression, lipid content, oxygen consumption rate, apoptosis can include (but it is not limited to) screening a library of candidate therapeutic agents (e.g., in a high-throughput multi-well format). The candidate therapeutic agents may be small molecules or any currently approved medication for each individual condition or any off label therapeutic agent.

One example of a method of identifying a therapeutic agent for preventing or treating proteinuric and glomerular disease (e.g., FSGS) in humans includes screening a library of potential therapeutic agents (e.g., small molecules) to identify one or more agents that inhibit podocyte cytoskeletal disruptions in a human. In a typical embodiment, the library is screened in a high-throughput multi-well format. The candidate therapeutic agents (e.g., compounds, candidate therapeutic agents, candidate agents, test compounds) can be any organic, inorganic, small molecule, protein, antibody, aptamer, nucleic acid molecule, or synthetic compound. Candidate compounds identified by assays described herein as useful pharmacological agents can be pharmacological agents already known in the art or variations thereof or can be compounds previously unknown to have any pharmacological activity. The candidate compounds can be naturally occurring or designed in the laboratory. Candidate compounds can comprise a single diastereomer, more than one diastereomer, or a single enantiomer, or more than one enantiomer.

Candidate or potential therapeutic agents may be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of e.g. bacterial, fungal and animal extracts are available or readily produced. The candidate or potential therapeutic agents can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive); spatially addressable parallel solid phase or solution phase libraries; synthetic library methods requiring deconvolution;

the one-bead one-compound library method; and synthetic library methods using affinity chromatography selection. Libraries of compounds may be presented in solution (e.g., Houghten (1992) Biotechniques 13:412-421), or on beads (Lam (1991) Nature 354:82-84), chips (Fodor (1993) Nature 364:555-556), bacteria (Ladner, U.S. Pat. No. 5,223,409), spores (Ladner U.S. Pat. No. 5,223,409), plasmids (Cull et al. (1992) Proc Nat'l Acad Sci USA 89:1865-1869) or on phage (Scott and Smith (1990) Science 249:386-390; Devlin (1990) Science 249:404-406; Cwirla et al. (1990) Proc. Natl. Acad. Sci. 87:6378-6382; Felici (1991) J. Mol. Biol. 222: 301-310).

One or more systems, methods or both can be used to identify a candidate or potential therapeutic agent for proteinuric and glomerular disease (e.g., FSGS). Manual systems/methods, semi-automated systems/methods, and automated systems/methods are all possible. A variety of robotic or automatic systems are available for automatically or programmably providing predetermined motions for handling, contacting, dispensing, or otherwise manipulating materials in solid, fluid liquid or gas form according to a predetermined protocol. Such systems may be adapted or augmented to include a variety of hardware, software or both to assist the systems in determining mechanical properties of materials. Hardware and software for augmenting the robotic systems may include, but are not limited to, sensors, transducers, data acquisition and manipulation hardware, data acquisition and manipulation software and the like. Exemplary robotic systems are commercially available from CAVRO Scientific Instruments (e.g., Model NO. RSP9652) or BioDot (Microdrop Model 3000).

Assays for Predicting if a Diabetic Subject Will Develop Kidney Disease

The assays described herein for predicting risk of primary or recurrent proteinuric glomerular disease (e.g., FSGS) can be modified as needed and used to predict if a diabetic subject will develop kidney disease. A typical assay for predicting if at least one diabetic subject will develop kidney disease includes: contacting a biological sample from the at least one diabetic subject with a first culture of human podocytes; examining the first culture of human podocytes for modulation (e.g., upregulation, downregulation, degradation of) of SMPDL-3b and/or any related lipid component, and/or particular cellular abnormalities such as cellular enlargement, cellular blebbing, loss of stress fibers, oxygen consumption rate and apoptosis; and correlating a presence of particular cellular abnormalities (e.g., cellular enlargement, cellular blebbing, loss of stress fibers, lipid accumulation, oxygen consumption rate and apoptosis) with an increased risk of development of kidney disease in the subject compared to a non-diabetic subject or a subject having diabetes without the kidney disease. Generally, the step of examining the first culture of human podocytes for particular cellular abnormalities (e.g., cellular enlargement, cellular blebbing, loss of stress fibers, lipid accumulation, oxygen consumption rate and apoptosis) includes determining a cytoskeletal phenotype of the first culture of human podocytes. This cytoskeletal phenotype can be compared to a cytoskeletal phenotype of a second culture of human podocytes that were contacted with a biological sample from at least one non-diabetic subject, or at least one diabetic subject who does not have the kidney disease (a negative control). The step of examining the first culture of human podocytes for cellular abnormalities (e.g., cellular enlargement, cellular blebbing and loss of stress fibers) is typically performed using confocal or light microscopy. However, any suitable device and/or means of examining the human podocytes for cellular abnormalities can be used. A disease-specific podocyte phenotype could be identified with the proposed assay for any other glomerular disorder (including those listed herein), and a specific prediction assay could be developed for each local or systemic disease.

Kits

A plurality of kits for performing assays and delivering treatments are described herein. A kit for determining if at least one subject who is at risk for a primary or secondary proteinuric glomerular disorder or who has a primary or secondary proteinuric glomerular disorder is at risk for primary or secondary disease development, progression or recurrence of the proteinuric glomerular disorder after kidney transplantation includes a plurality of reporter cells comprising a vector containing a nucleic acid encoding the SMPDL-3b promoter sequence operably linked to a nucleic acid encoding a reporter gene; at least one control; and instructions for use. In an alternative embodiment, a kit for determining if at least one subject who is at risk for a primary or secondary proteinuric glomerular disorder or who has a primary or secondary proteinuric glomerular disorder is at risk for primary or secondary disease development, progression or recurrence of the proteinuric glomerular disorder after kidney transplantation includes at least one container of podocytes; cytochalasin D as a positive control; a dye for actin cytoskeleton; and instructions for use. In addition to or alternatively to cytochalasin D, any suitable positive control can be used. Such positive controls are known in the art. A kit for predicting a response in at least one subject to at least one candidate therapeutic agent for treatment or prevention of a particular proteinuric glomerular disease includes a plurality of reporter cells including a vector containing a nucleic acid encoding the SMPDL-3b promoter sequence operably linked to a nucleic acid encoding a reporter gene; a plurality of candidate therapeutic agents; at least one control; and instructions for use. In an alternative embodiment, a kit for predicting a response in at least one subject to at least one candidate therapeutic agent for treatment or prevention of a particular proteinuric or glomerular disease includes at least one container of podocytes; cytochalasin D as a positive control; a dye for actin cytoskeleton; a plurality of candidate therapeutic agents; and instructions for use.

In some embodiments, kits are provided for determining if a subject is at risk for primary glomerulopathy, secondary glomerulopathy or post-transplant recurrence of any glomerular disease (FSGS, DN, Membranous nephropathy, minimal change disease, IgA nephropathy, Membranoproliferative glomerulopathy, lupus nephritis, myeloma kidney, hypertensive nephrosclerosis, paucimmune glomerulonephritis, amyloidosis, cryoglobulinemia, thrombotic thrombocytopenic purpura, Hemolytic uremic syndrome, scleroderma kidney, Alport's glomerulopathy, transplant glomerulopathy, storage disorders and other rare genetic disorders). Such kits can be used, for example, to determine if at least one subject (e.g., human) who has FSGS is at risk for recurrent FSGS after kidney transplantation. A typical kit for determining if at least one subject (e.g., human) who has a proteinuric and glomerular disease (e.g., FSGS) is at risk for recurrent proteinuric and glomerular disease (e.g., recurrent FSGS) after kidney transplantation includes a plurality of podocytes, at least one control (e.g., negative control, positive control), and instructions for use. In one embodiment, a kit includes a vial of podocytes, a set of Cytochalasin D vials at different concentrations to be utilized for a standard curve, and instructions for use/protocols for treatment and media preparation.

In the kits, any suitable controls and reagents for generating standard curves may be used. Cytochalasin D is just one example of a regent for generating a standard curve, and others may be used. Similarly, in addition to a dye for actin cytoskeleton, any marker or label suitable for examining or visualizing the actin cytoskeleton may be used (e.g. phalloidin, anti F actin antibodies). Any of the kits may include a collagen coated well plate to carry a mixture of the different reagents, as well as one or more washing buffers. Optionally, kits may also contain one or more of the following: containers which include positive controls, containers which include negative controls, photographs or images of representative examples of positive results and photographs or images of representative examples of negative results. Kits may also include reagents for the determination of podocyte lipid content, apoptosis, and oxygen consumption rate when considered appropriate for a specific proteinuric glomerular disease.

Compositions and Methods for Preventing or Treating Proteinuric and Glomerular Diseases Compositions and methods for preventing and/or treating proteinuric and glomerular diseases or disorders (e.g., FSGS, DN, Membranous nephropathy, minimal change disease, IgA nephropathy, Membranoproliferative glomerulopathy, lupus nephritis, myeloma kidney, hypertensive nephrosclerosis, paucimmune glomerulonephritis, preeclampsia, amyloidosis, cryoglobulinemia, thrombotic thrombocytopenic purpura, Hemolytic uremic syndrome, scleroderma kidney, Alport's glomerulopathy, storage disorders and other rate genetic disorders) in a subject are described herein. Using the screening assays and platforms described herein, one or more therapeutic agents for preventing and/or treating a proteinuric or glomerular disorder can be identified. In one embodiment of a method of preventing and/or treating a proteinuric or glomerular disorder (e.g., recurrent FSGS) in a subject, the method includes providing a composition including an agent that restores physiological expression of SMPDL-3b, lipid content, oxygen consumption rate or apoptosis, thus driving personalized therapeutic decisions about which composition to administer to the subject in a therapeutically effective amount for preventing and/or treating the proteinuric or glomerular disorder (e.g., recurrent FSGS) in the subject. In one example, the agent that upregulates activity and/or expression of SMPDL-3B is rituximab, a chimeric antibody directed against CD20 that has been developed for the cure of lymphoma and that has been found to bind SMPDL-3B as well (Perosa F, Favoino E, Caragnano M A, Dammacco F. Blood 2006; 107(3):1070-7). A method of preventing and/or treating recurrent FSGS in a subject may include administering to the subject a composition including an agent that increases SMPDL-3b levels or restores cytoskeleton rearrangements and a pharmaceutically acceptable carrier, wherein the composition is administered to the subject having FSGS in an amount effective to prevent or treat FSGS in the subject. For example, a drug such as abatacept can be administered to the subject. In Example 4 below (FIGS. 4A-4C), clinical tests are described in which abatacept reversed early post-transplant recurrent proteinuria in at least one patient with previous recurrent FSGS.

The screening assays and platforms described herein may find particular use in identifying therapeutic agents known for treating disorders other than proteinuric and glomerular disorders that are useful also for preventing and/or treating a proteinuric or glomerular disorder. Such off label use of drugs (e.g., abatacept, rituximab) for treating a proteinuric or glomerular disorder is exemplified in the Examples section below.

Compositions and Methods for Preventing and/or Treating Renal Diseases that Modify Cellular Lipid Content Described herein are methods of administering cyclodextrin or its derivatives, or any drug lowering the plasma membrane or cellular cholesterol/lipid content, to a patient for a time and under conditions sufficient to prevent, treat, cure, or reverse renal-related disorders. It is known that elevated cholesterol levels, and in particular low-density lipoprotein (LDL) cholesterol, in the plasma play an important role in the development of kidney disease and other renal-related diseases. Currently available treatments to lower cholesterol levels in patients, however, aim to lower plasma cholesterol levels (LDL) by blocking the synthesis of cholesterol in the liver (statins), by preventing reabsorption of cholesterol into the circulatory system (bile acid resins, cholesterol absorption inhibitors), or by increasing HDL cholesterol (fibrates, niacin derivatives). None of the currently used medications aims on lowering plasma membrane or cellular cholesterol/lipid.

A typical method of preventing or treating a renal-related disorder in a subject includes administering to the subject a composition including one or more of: a cyclodextrin, a cyclodextrin derivative, and a cellular cholesterol-lowering agent that is not a statin (alone or in combination with other drugs currently used to treat the subject for a renal-related disorder). The composition is administered to the subject in an amount effective for reducing one or more of: plasma membrane cholesterol, plasma membrane lipids, cellular cholesterol, and cellular lipids in the subject. Typically, the composition is administered in an amount effective for preserving podocyte function and preventing proteinuria in the subject. Additionally, administration of the composition may result in reduction of plasma membrane cholesterol, cellular cholesterol, or cellular lipids in podocytes of the kidney of the subject. Examples of renal-related diseases include primary glomerulopathy, secondary glomerulopathy, or a post-transplant recurrence of a glomerular disease (e.g., FSGS, Membranous nephropathy, minimal change disease, IgA nephropathy, Membranoproliferative glomerulopathy, diabetic nephropathy, lupus nephritis, myeloma kidney, hypertensive nephrosclerosis, paucimmune glomerulonephritis, preeclampsia, amyloidosis, cryoglobulinemia, thrombotic thrombocytopenic purpura, Hemolytic uremic syndrome, scleroderma kidney, Alport's glomerulopathy, transplant glomerulopathy storage disorder, stroke, peripheral vascular disease, diabetes, coronary artery disease, congestive heart failure, cardiac hypertrophy, myocardial infarction, endothelial dysfunction and hypertension). In the method, the composition can further include a drug such as: an immunosuppressive agent, an ACTH agonist, an insulin sensitizer, a GH antagonist, an antinflammatory medication, a vitamin D derivative, a RAS system inhibitor, an aldosterone inhibitor, an HMG-CoA reductase inhibitor, a cholesterol absorption inhibitor, a bile acid sequestrant, a bile acid resin, Niacin, a Niacin derivative, a fibrate, a cholesteryl ester transfer protein (CETP) inhibitor, an Acetyl- Coenzyme A acetyltransferase (ACAT) inhibitor, and a microsomal triglyceride transport inhibitor.

One embodiment of a method of treatment relates to renal-related disorders such as proteinuric diseases, albuminuric diseases, Diabetic nephropathy, Nephrotic or Nephritic syndromes, Toxic lesions of the kidneys, glomerular diseases such as FSGS, IgA or IgM nephropathy, Membranoproliferative glomerulonephritis, Membranous nephropathy, Minimal change disease, Hypertensive nephrosclerosis or Interstitial nephritis. In another embodiment, a renal-related disorder can be, for example, stroke, peripheral vascular disease, coronary artery diseases, congestive heart failure, cardiac hypertrophy, myocardial infarction, endothelial dysfunction and hypertension. In a typical embodiment, the drug used to prevent, treat, cure or reverse renal-related disorders is any drug that lowers the plasma membrane and cellular cholesterol/lipid content of the cell. The drug can hereby be administered to an individual in a variety of ways. Routes of administration include, intramuscular, intraperitoneal, intravenous (systemic), subcutaneous, transdermal, oral, topical, and intranasal routes. The drug can be administered together with other biologically active agents or components as pharmaceutically acceptable carriers, diluents, excipients and vehicles. In one embodiment, the drug used to prevent, treat, cure or reverse renal-related disorders is Cyclodextrin or any of its derivatives. In another embodiment, Cyclodextrin is used to prevent, treat or reduce proteinuria in patients.

Also described herein are methods of reducing the plasma membrane or cellular cholesterol/lipid content in any cells of any organ as a tool to prevent, treat, cure or reverse renal-related disorders. In one embodiment, the plasma membrane or cellular cholesterol/lipid content is reduced in any cell of the kidney as a tool to prevent, treat, cure or reverse renal-related disorders. In another embodiment, the plasma membrane or cellular cholesterol/lipid content is reduced in podocytes of the kidney as a tool to prevent, treat, cure or reverse renal-related disorders. In another embodiment, Cyclodextrin or its derivatives are used to at least partially deplete kidney cells from cholesterol/lipid alone or in combination with other drugs currently used or being studied for the prevention and the treatment of kidney-related diseases such as immunosuppressive agents, ACTH agonists, insulin sensitizers, GH antagonists, antinflammatory medications, vitamin D derivatives, blockers of the RAS system and of aldosterone. In another embodiment, Cyclodextrin, its derivatives, or any other plasma membrane or cellular cholesterol/lipid lowering drug is used in combination with a cholesterol biosynthesis inhibitor, such as a HMG-CoA reductase inhibitor. HMG-CoA reductase inhibitor drugs include drugs such as Simvastatin, Atorvastatin, Lovastatin, Rosuvastatin, Pravastatin, Fluvastatin, Pitavastatin, Rosuvastatin, Rivastatin, Itavastatin, or ZD-4522. In another embodiment, Cyclodextrin, its derivatives, or any other plasma membrane or cellular cholesterol lowering drug is used in combination with a cholesterol absorption inhibitor, such as a Ezetimibe, SCH-48461. In another embodiment, Cyclodextrin, its derivatives, or any other plasma membrane or cellular cholesterol/lipid lowering drug is used in combination with bile acid sequestrants and resins (Colestipol, Colestilan, Colextran, Cholestyramine, Colesevelam). In another embodiment, Cyclodextrin, its derivatives, or any other plasma membrane or cellular cholesterol/lipid lowering drug is used in combination with Niacin and Niacin derivatives such as Niceritrol, Nicotinyl alcohol, Acipimox. In another embodiment, Cyclodextrin, its derivatives, or any other plasma membrane or cellular cholesterol/lipid lowering drug is used in combination with fibrates such as Fenobrate, Clinofibrate, Etofibrate, Bezafibrate, Gemfibrozil. In another embodiment, Cyclodextrin, its derivatives, or any other plasma membrane or cellular cholesterol/lipid lowering drug is used in combination with cholesteryl ester transfer protein (CETP) inhibitors such as Dalcetrapib, Anacetrapib. In another embodiment, Cyclodextrin, its derivatives, or any other plasma membrane or cellular cholesterol/lipid lowering drug is used in combination with Acetyl-Coenzyme A acetyltransferase (ACAT) inhibitors (such as avasimibe) or microsomal triglyceride transport inhibitors.

These combination treatments may also be effective for the treatment or control of one or more renal-related conditions such as atherosclerosis, insulin resistance, hyperlipidemia, hypertriglyceridemia, dyslipidemia, high LDL, and low HDL.

Data and Analysis

Use of the assays, methods and kits described herein may employ conventional biology methods, software and systems. Useful computer software products typically include computer readable medium having computer-executable instructions for performing logic steps of a method. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, for example Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001). See U.S. Pat. No. 6,420,108.

The assays, methods and kits described herein may also make use of various computer program products and software for a variety of purposes, such as reagent design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170. Additionally, the embodiments described herein include methods for providing data (e.g., experimental results, analyses) and other types of information over networks such as the Internet.

Additional Embodiments

It should be clear from the present disclosure that the assays and kits described herein include screening individuals without kidney disease for disease development, as well as screening individuals with kidney disease for disease progression or recurrence after transplant (e.g., kidney transplant). Such screening can be done using the protocols, methods, reagents, kits and assays described herein.

An assay for determining if at least one subject who has FSGS is at risk for recurrent FSGS after kidney transplantation may include: contacting a biological sample from the at least one subject with a culture of human podocytes; examining the podocytes for the presence or absence of cytoskeletal disruptions or rearrangements, lipid accumulation, modulation of physiological SMPDL-3b levels, and or apoptosis resulting in determination of a first phenotype of the podocytes; and correlating a presence of cytoskeletal disruptions or rearrangements of stress fibers with an increased risk of FSGS recurring in the subject subsequent to a kidney transplantation compared to subjects without recurrent FSGS. In the assay, the biological sample (e.g., blood, saliva, serum, plasma, tissue, and urine) can be obtained prior to the kidney transplantation and initiation of immunosuppression in the subject. The cytoskeletal disruptions or rearrangements (e.g., disruption of stress fibers) can be examined by the methods described herein. The assay can further include comparing the cytoskeletal phenotype of human podocytes with the quantitative determination of cholesterol/lipid accumulation, modulation of SMPDL-3b, and/or apoptosis. In some embodiments, the subject has an increased risk of FSGS recurring subsequent to a kidney transplantation compared to subjects without recurrent FSGS, and the assay further includes making a quantitative assessment of an FSGS phenotype. The assay can further include comparing the first phenotype with a second phenotype of podocytes contacted with a biological sample from at least one normal subject, and a third phenotype of podocytes contacted with a biological sample from at least one subject with recurrent FSGS. The second phenotype is typically a negative control, and the third phenotype a positive control. The at least one subject (e.g., pediatric and/or African American) can be a plurality of subjects who have FSGS. In some assays, a standard curve is analyzed. The step of examining the podocytes for the presence or absence of cytoskeletal disruptions or rearrangements resulting in determination of a first phenotype of the podocytes can include counting the number of podocytes that display cytoskeletal disruptions or rearrangements. Generally, at least one subject who is at risk for development of recurrent FSGS is identified prior to the at least one subject receiving a kidney transplant.

An assay for predicting if at least one diabetic subject will develop kidney disease (e.g., diabetic nephropathy, proteinuric kidney disease, etc.) includes: contacting a biological sample from the at least one diabetic subject with a first culture of human podocytes; examining the first culture of human podocytes for cellular enlargement, cellular blebbing, cortical distribution of the actin cytoskeleton stress fibers, modulation of SMPDL-3b, lipid accumulation, oxygen consumption rate and apoptosis; and correlating the presence of one or more of: cellular enlargement, cellular blebbing and cortical distribution of the actin cytoskeleton stress fibers, modulation of physiological SMPDL-3b levels, cholesterol/lipid accumulation, increased oxygen consumption rate and apoptosis with an increased risk of development of kidney disease in the subject compared to a non-diabetic subject or a subject having diabetes without the kidney disease. The step of examining the first culture of human podocytes for cellular enlargement, cellular blebbing, loss of stress fibers can include determining a cytoskeletal phenotype of the first culture of human podocytes. The assay can further include comparing the cytoskeletal phenotype of the first culture of human podocytes with a cytoskeletal phenotype of a second culture of human podocytes that were contacted with a biological sample from at least one non-diabetic subject, or at least one diabetic subject who does not have the kidney disease. The assay can further include comparing the cytoskeletal phenotype of human podocytes with the quantitative determination of cholesterol/lipid accumulation, modulation of physiological SMPDL-3b levels, increased oxygen consumption rate and apoptosis. The step of examining the first culture of human podocytes for cellular enlargement, cellular blebbing and cortical distribution of the actin cytoskeleton stress fibers can be performed using any suitable method, e.g., confocal or light microscopy.

A method of identifying a therapeutic agent for preventing or treating recurrent FSGS in at least one subject includes: culturing human podocytes in the presence of a biological sample from at least one subject with recurrent FSGS; contacting the podocytes with one or more candidate therapeutic agents; examining the podocytes for cytoskeletal disruptions; and identifying agents which prevent or decrease cytoskeletal disruptions. The steps of contacting the podocytes with one or more candidate therapeutic agents, examining the podocytes for cytoskeletal disruptions; and identifying agents which prevent or decrease cytoskeletal disruptions can include screening a library of candidate therapeutic agents (e.g., in a high-throughput multi-well format). The candidate therapeutic agents may be small molecules or any currently approved medication for each individual condition. The candidate therapeutic agents can also be off label drugs. The method described herein may therefore allow for the identification of personalized treatment strategies for any patient with any renal disorder.

A method of preventing or treating recurrent FSGS in a subject includes the steps of: providing a composition including an agent that upregulates activity and/or expression of SMPDL-3b; and administering the composition to the subject in a therapeutically effective amount for preventing recurrent FSGS in the subject. The agent can be, for example, an antibody that stabilizes cellular membranes and prevents degradation of cellular membranes. Additional examples of agents include nucleic acid, proteins, polypeptides, compounds, off-label drugs, extracts, cells, etc. A method for preventing or treating DN may involve agents that affect podocyte function through the modulation of cellular cholesterol/lipid content (e.g., sterols, sphingolypids, triglyceride, free fatty acids, glycosphingolypids, ceramide). Therefore, any agent capable of modulating podocyte SMPD1-3b or any lipid related protein (ASMase, S1P, ABCA1, ABCG1, LDL-rec, ACC1, fatty acid synthase, stearoyil-CoA desaturase, HMG-CoA reductase, SERBPs) can be utilized for the prevention and the cure of DN and of any other proteinuric renal disorder.

EXAMPLES

The present invention is further illustrated by the following specific examples. The examples are provided for illustration only and should not be construed as limiting the scope of the invention in any way.

Example 1—Assay for the Prediction of Recurrent FSGS after Kidney Transplantation Shown in FIG. 1A are representative stress fiber confocal images of normal human podocytes exposed to normal (NHS) (n=5), non-recurrent (NON-REC) FSGS (n=10), and recurrent (REC) FSGS (n=12) human sera. Shown in FIG. 1B is the percentage of cells with disruption of stress fibers observed after exposure to NHS (n=5), non-recurrent sera (n=10), and recurrent human sera (n=12). FIG. 1C shows the linear correlation between the percentage of cells with loss of stress fibers and the urine protein/creatinine ratio obtained from REC and NON-REC patients (n=22) in the first 30 days after transplantation. Shown in FIG. 1D are confocal images of stress fibers and corresponding bar graph analysis of normal human podocytes exposed to recurrent FSGS sera in the presence (REC+RITUX) or absence (REC) of rituximab. Rituximab protected the loss of stress fibers observed in stressed podocytes exposed to recurrent FSGS, but not non-recurrent FSGS human sera. Shown in FIG. 1E are confocal images of stress fibers and corresponding bar graph analysis of normal human podocytes exposed to REC sera transfected with an empty GFP vector (REC) or with a SMPDL-3b-GFP vector (REC+SMPDL-3b). SMPDL-3b overexpression protected the loss of stress fibers observed in podocytes exposed to recurrent FSGS human sera. The presented in vitro studies strongly correlate with in vivo clinical outcome data, as rituximab administered in patients at high risk for recurrent FSGS after transplantation significantly protected from the development of post transplant proteinuria as demonstrated in Table 1.

TABLE 1

Patient demographics and clinical outcome.

|  | Controls (No rituximab) N = 14 | Treated (Rituximab) N = 27 | p value |
|---|---|---|---|
| Age (mean ± SD) | 12.3 ± 5.2 | 15.0 ± 5.5 | 0.1650 |
| Race (W/B) | 9/5 (64%/36%) | 14/13 (52%/48%) | 0.5203 |
| Gender (M/F) | 6/8 (43%/57%) | 9/18 (33%/67%) | 0.7337 |
| Time to ESRD (year) | 3.3 ± 2.1 | 3.4 ± 2.0 | 0.7942 |
| Donor (LD/DD) | 9/5 (64%/36%) | 4/23 (15%/85%) | 0.0033* |
| Donor age (mean ± SD) | 31.3 ± 9.4 | 24.7 ± 14.6 | 0.1290 |
| Nephrectomy (Y/N) | 7/7 (50%/50%) | 16/11 (59%/41%) | 0.7417 |
| Nephrotic proteinuria w/i 1 Mo | 9 (64%) | 7 (26%) | 0.229* |
| Plasmapheresis w/I 1 Mo | 10 (71%) | 8 (30%) | 0.0192* |
| CD 19 count |  |  |  |
| Week 0 | 412 ± 223 | 360 ± 223 | 0.4344 |
| Week 0.5 | 327 ± 290 | 107 ± 115 | 0.0145* |
| Week 1 | 472 ± 437 | 45 ± 31 | <0.0001* |
| Week 2 | 559 ± 526 | 16 ± 23 | <0.0001* |
| Week 3 | 729 ± 670 | 5 ± 6 | <0.0001* |
| Week 4 | 630 ± 384 | 6 ± 7 | 0.0002* |
| ΔeGFR (vs. 1 mo nadir) |  |  |  |
| 3 months | −18.0 ± 16.9 | −1.3 ± 14.6 | 0.0012* |
| 6 months | −19.0 ± 19.8 | −5.3 ± 18.4 | 0.0075* |
| 12 months | −26.9 ± 26.7 | −20.3 ± 27.3 | 0.3717 |
| Graft survival |  |  |  |
| 6 months | 92.9% | 100% | 0.1730 |
| 12 months | 85.7% | 95.8% | 0.2639 |

Age, race, gender, nephrectomy of the native kidneys, time to ESRD and donor characteristics are shown for the 14 historical control patients compared to the 27 patients that received one dose of rituximab (375 mg/m$^2$) within 24 hours of transplant. CD19+ cells significantly decreased in treated patients 0.5 weeks after infusion and were almost undetectable 1 week after treatment. The incidence of recurrent nephrotic range proteinuria and need for plasmapheresis between day 3 and 30 after transplantation was significantly lower in the rituximab group than in the control group. The changes of estimated GFR (ΔeGFR) at 3-6 months from baseline at 1 month post-transplant were significantly worse in control group than rituximab group. There was no significant difference in graft survival between groups at 6 and 12 months. W=white, B=black, M=male, F=female, ESRD=end stage renal disease, LD=living donor, DD=deceased donor. ΔeGFR: variation of eGFR. *p<0.05.

Example 2—Rituximab and/or SMPDL-3b Upregulation has a Protective Effect in FSGS FIGS. 2A-2G demonstrate that the modulation of SMPDL-3b in kidney biopsies and in podocytes cultured in the presence of patient sera can be predictive of recurrence of FSGS after transplantation. (A) Low- and high-power images of immunoperoxidase staining for SMPDL-3b and synaptopodin in post-reperfusion biopsies of patients with recurrent (REC) and non-recurrent (NON-REC) FSGS. Arrows point to podocytes. (B) The number of SMPDL-3b+ podocytes per glomerulus, as evaluated by SMPDL-3b and synaptopodin labeling in post-reperfusion kidney biopsies from patients that later on developed recurrent (REC) disease (n=8) and patients that did not develop clinical recurrence (NON-REC) (n=12). All kidney biopsies were obtained prior to initiation of treatment with rituximab. (C) Regulation of podocyte SMPDL-3b mRNA expression by normal (NHS), non-recurrent (NON-REC) FSGS, and recurrent (REC) FSGS human sera (n=4 per group) and by rituximab. (D) The amount of SMPDL-3b protein is normalized to actin in human podocytes treated with normal (n=5), recurrent (n=12), or non-recurrent (n=10) human sera and exposed to rituximab. (E) Western blot for SMPDL-3b protein of normal podocytes cultured with sera from consecutive non-recurrent (n=4) and recurrent (n=4) FSGS patients in the presence or absence of rituximab. (F) The amount of 52 and 54 kDa ASMase protein is normalized to actin in human podocytes that were exposed to normal (n=5), non-recurrent FSGS (n=10), and recurrent FSGS (n=12) human sera in the presence or absence of rituximab. (G) ASMase activity per μg of total lysate protein, as evaluated by ELISA.

Referring to FIGS. 2A-2G and Table 1, experiments were performed that demonstrate that rituximab and SMPDL-3b overexpression equally protect podocytes from REC sera-induced disruption of stress fibers. Rituximab (Perosa F, Favoino E, Caragnano M A, Dammacco F. Blood 2006; 107(3):1070-7) is a chimeric antibody directed against CD20 that has been developed for the cure of lymphoma and that has been found to bind SMPDL-3B as well (Perosa F, Favoino E, Caragnano M A, Dammacco F. Blood 2006; 107(3):1070-7). Therefore, the assay proposed herein could be utilized not solely as a prediction assay for recurrent disease but also as a pre-transplant assay to determine which drug, if any, would be more efficient in preventing recurrent proteinuria in a given patient. It is expected that drugs administered to podocytes in vitro prior or after sera exposure may protect stress fibers formation, similar to what has been shown for Rituximab in FIGS. 1A-1E. This assay could therefore offer a pre-transplant measure of the ability of a given patient to respond to a given drug after transplantation.

Example 3—Assay for the Prediction of Diabetic Nephropathy

Figure 3D:
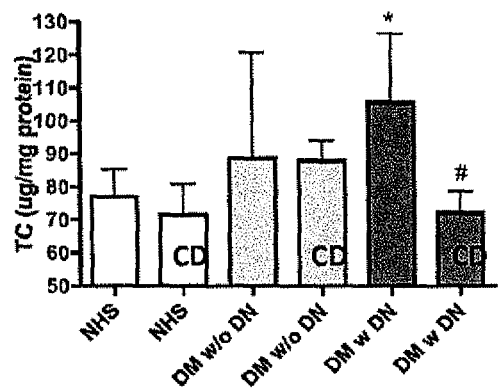
Figure 3E:
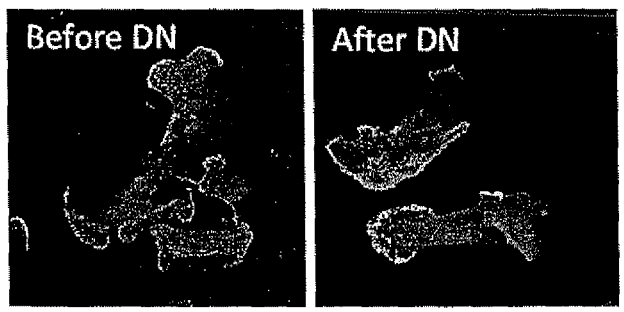
Figure 3F:
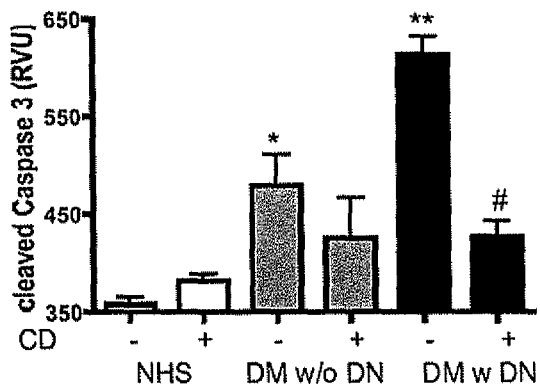

DN is a chronic progressive disease that affects a sizable subset of patients with diabetes. Despite the identification of multiple risk factors that contribute to the development of DN, it has remained difficult to identify the subset of patients with diabetes at risk for DN. This led to testing to determine if an in vitro prediction assay could be developed. For this purpose, the following experiments were conducted. Non-identifiable samples of patient sera were obtained. Samples consisted of serum collected from 10 patients with diabetes and macroalbuminuria (DM w DN) and 10 diabetic normoalbuminuric patients (DM w/o DN) well matched for HgA1$_C$ (7.9%), total cholesterol levels and the duration of diabetes. Normal human sera (NHS) from 10 age and sex matched healthy subjects were also utilized as controls. Differentiated human podocytes were serum starved for 24 hours and then exposed to 4% serum of NHS, DM w/o DN, DM w DN for 24 hours. After a brief fixation with 4% PFA, immunostainings for F-actin and DAPI were performed and demonstrated that DM w DN sera treated podocytes experienced a pronounced actin cytoskeleton meshwork with localized decoupling of the cytoskeleton from the plasma membrane (blebbing), which was evident in both, the phalloidin staining as well as in the brightfield images (FIG. 3A). Quantitative analysis of the cell blebbing (percentage of cells with blebs out of a total of 200 cells analyzed) revealed this phenotype in 80% of cells exposed to sera of the DM w DN group as compared to only 20% in the cells exposed to DM w/o DN and 5% in the NHS (FIG. 3B, p<0.01). Although filipin staining revealed increased cellular cholesterol in cells exposed to both DM w/o DN and DM w DN sera, this was particularly pronounced in the DM w DN group, where it was accompanied by a redistribution of phosphorylated caveolin (utilized as a marker of focal adhesion contact) to blebs, a phenomenon that could be prevented by cyclodextrin (CD) (FIG. 3C). Total cholesterol was also determined with an enzymatic reaction. Total cholesterol was increased in podocytes treated with DM w DN when compared to DM w/o DN and NHS (FIG. 3D, *p<0.05), a phenomenon that was prevented by CD (FIG. 3D, #p<0.05). Cell blebbing was predictive of DN, as sera collected from patients before progressing to DN at the time they were normoalbuminuric already caused cell blebbing (FIG. 3E). DM w DN sera also resulted in increased podocyte apoptosis (FIG. 3F, *p<0.05, **p<0.01), a phenomenon that could be prevented by CD (FIG. 3F, #p<0.05). Taken together, these data suggest that it is possible to develop an in vitro assay to screen patients with diabetes for their risk to develop DN.

Example 4—Use of Abatacept to Reverse Early Post-Transplant Recurrent Proteinuria in Patients with Established Recurrent FSGS Described herein for the first time, is the successful use of abatacept and plasmapheresis to reverse post-transplant early recurrent proteinuria in two patients with a second allograft with a history of previous recurrent FSGS. A post-reperfusion kidney biopsy demonstrated damage to podocytes (electron microscopy) not present on the pre-perfusion biopsy. The response to abatacept was associated with the podocyte specific appearance of B7-1/CD80 expression on the post-reperfusion renal biopsy when compared to the pre-perfusion biopsy, similar to what has been reported in patients with proliferative lupus nephritis (FIGS. 4A-4C). This case report highlights the possible role of B7-1/CD80 in the pathogenesis of recurrent FSGS and offers a novel rationale for the utilization of Anti-B7-1/CD80 therapy in this setting.

Case Report 1

A 28-year old woman who was diagnosed with FSGS with mesangial proliferation presented with nephrotic range proteinuria at the age of 16 years. Despite aggressive treatment with high dose steroids, tacrolimus, angiotensin converting enzyme inhibitor and angiotensin-2 receptor blocking therapy, she developed ESRD within 7 years of FSGS diagnosis. While she was on haemodialysis, she underwent medical nephrectomy by using high-dose nonsteroidal anti-inflammatory agents to reduce her severe proteinuria. Two months after starting dialysis, she underwent one-haplotype-matched living related renal transplant at 23 years old from her 53-year-old father. She received Thymoglobulin (1 mg/kg×5 doses), daclizumab (1 mg/kg×2 doses) and methylprednisolone as induction therapy, 1 dose of rituximab (375 mg/m²) and plasmapheresis. Renal function recovered after transplantation with mild postoperative proteinuria that responded to plasmapheresis. The immunosuppression was maintained with tacrolimus, mycophenolatemofetil and steroids. Approximately 18 months after transplant, she presented with bilateral lower limb edema and significant proteinuria (7 gm/24 hrs) along with hypoalbuminemia and elevated serum creatinine (2.1 mg/dl). Renal transplant biopsy demonstrated recurrent FSGS. In the following months, the renal function continued to deteriorate. The renal graft failed approximately 28 months after the transplant due to recurrent FSGS and chronic transplant glomerulopathy. She was maintained on dialysis until approximately 3 years after the transplant when she received a second living-related donor kidney transplant, this time from her aunt. She had pre-transplant plasmapheresis followed by daclizumab, methylprednisolone and Thymoglobulin induction. She received a single dose of rituximab within 24 hours of transplant. Kidney transplant biopsies were obtained in the operating room after the kidney was flushed (pre-perfusion biopsy) with lactated ringer's solution (with added heparin, solu-medrol, sodium bicarbonate and lidocaine) and 2 hours post-reperfusion of the kidney. An external stent (from renal pelvis, into bladder, exiting through the abdominal wall) was placed in the newly transplanted kidney to differentiate urine from the second transplant from the previously transplanted kidney.

The newly transplanted kidney began to make urine immediately but spot urinalysis obtained from the new allograft immediately post operatively showed increased urinary protein to creatinine ratio. Her creatinine stabilized by the 3rd day post transplant to between 1.2 and 1.5 mg/dl. There was no evidence of reperfusion injury, acute tubular necrosis, cellular rejection, vascular rejection or glomerulosclerosis on the formalin fixed post-reperfusion biopsy. However, there was effacement of the foot processes and enlargement of the podocytes noted on the post-reperfusion biopsy examined by electron microscopy. Pre and post-reperfusion renal biopsies were also examined by immunofluorescencestudy of B7-1/CD80. Pre and post-reperfusion biopsies were embedded in OCT. Ten mm-thick sections were fixed for 10 minutes in cold acetone and blocked in 10% goat serum for 30 minutes. Slides were incubated with a goat anti-human B7.1/CD80 antibody (15 g/ml, R&D Systems, Minneapolis, Minn.) and with a mouse monoclonal antibody against the podocyte protein synaptopodin (Mundel et al., J Cell Biol vol. 139:193-204, 1997) (Byodesign International, 1:100), followed by exposure to Alexa-488 secondary donkey anti-goat and Alexa-647 anti-mouse antibodies (dilution of 1:200, Invitrogen). An irrelevant antibody isotype was used as negative control. Image acquisition was performed with Leica SP5 inverted confocal microscope. The pre-reperfusion staining was negative for B7-1/CD80; however, the immunohistological studies showed positive staining with B7-1/CD80 in the post-reperfusion biopsywith partial colocalization with synaptopodin utilized as a specific podocyte marker. Since immediate FSGS recurrence was highly suspected, a course of 4 sessions of alternative day plasmapheresis with simultaneous administration of 1 dose of Abatacept (500 mg) was started on postoperative day (POD) 3. After peaking at 4.6, the urinary protein to creatinine ratio decreased progressively. Correspondingly, the serum albumin and total protein levels increased to normal values. She was discharged with tacrolimus, rapamycin (due to mycophenolate mofetil intolerance), irbesartan and eplerenoneon POD 8 with a random urinary protein to creatinine ratio 0.8 mg/mg. The patient underwent one more session of plasmapheresis in the outpatient clinic. Since then (1.5 years after cessation of plasmapheresis and abatacept treatment) she remained stable with creatinine levels of 1.3 mg/dl, and mild proteinuria with a normal serum albumin.

Case Report 2

A 16-year-old white Hispanic female was diagnosed at the age of 18 months with FSGS. She was treated for severe cardiomyopathy and steroid-resistant nephrotic syndrome, which progressed to ESRD over the course of 7 years. She subsequently underwent native bilateral nephrectomy at the age of 8 years and the first kidney transplantation at the age of 9 years from her 41-year-old mother with Thymoglobulin and daclizumab induction, and tacrolimus, mycophenolate and corticosteroids maintenance therapy. She developed massive proteinuria (urine protein/creatinine ratio >40) 2 days after the transplantation requiring plasmapheresis and angiotensin receptor blocker therapy. She continued to be nephrotic with gradual deterioration of renal function, especially after she developed acute rejection at 13 months post-transplant; the renal transplant biopsy at that time revealed recurrent FSGS, IA acute T-cell-mediated rejection, moderate interstitial fibrosis/tubular atrophy, and calcineurin-inhibitor toxicity. She eventually lost her first graft function 4.5 years after the transplantation and returned to dialysis therapy. While waiting for the second kidney transplantation, she developed latent tuberculosis, which required a 9-month isoniazid treatment. She was highly sensitized, but the degree of sensitization fell spontaneously from PRA of 60% to 20%, and she received her second kidney transplantation from a 34-year-old deceased donor. The transplant procedure went uneventfully with an external ureteral stent placement to distinguish urine of the second transplant kidney from the first transplant. The patient received induction therapy with Thymoglobulin (1 mg/kg×5 doses) and basiliximab (20 mg×2 doses), as well as a single dose of rituximab (375 mg/m$^2$), and was maintained on tacrolimus, mycophenolic acid and corticosteroids. As depicted in FIGS. 4A-4C, the kidney allograft presented immediate function; however, spot urine revealed significant proteinuria (protein/creatinine ratio 9-17), suggesting early recurrence of FSGS. During the initial hospital stay, 6 sessions of plasmapheresis were performed without significant improvement in urine protein levels. A single dose of abatacept (500 mg) was administered on POD 9. She was discharged on POD 10 with above maintenance immunosuppression and candesartan. She had 3 additional sessions of plasmapheresis in the outpatient clinic. Subsequent to receiving abatacept, there was a marked decreased in urine protein levels. Currently, at 3 months post-transplant, the patient has a serum creatinine level of 0.7 mg/dl and a urine protein/creatinine ratio of 1.3.

In these trials, podocyte foot process effacement and swelling was noted by EM in the post-reperfusion biopsy consistent with early recurrent FSGS. This is the first demonstration of expression of B7-1/CD80 on podocytes in post-reperfusion biopsies in patients with post-transplant proteinuria associated with recurrent FSGS immediately post-transplant. The recurrent FSGS proteinuria was treated with abatacept combined with plasmapheresis, angiotensin converting enzyme and angiotensin II receptor blocker based on a clinical diagnosis of presumed recurrence.

The results of these trials suggest that the expression of B7-1/CD80 in podocytes may be induced immediately post-reperfusion in patients at high risk for recurrent FSGS. Both patients responded to a combination of plasmapheresis and abatacept. In the second case, the reduction in proteinuria was temporally associated with the administration of abatacept. Abatacept may be effective in reducing proteinuria and progression of recurrent glomerulosclerosis. If additional studies confirm a critical role for B7-1/CD80 in the pathogenesis of early proteinuria following kidney transplant for FSGS, abatacept could be utilized for pre-emptive therapy to avoid the recurrence by virtue of its direct effect on the podocyte.

Example 5—Modulation of SMPDL-3b Affects Podocyte Cholesterol/Lipid Content

Figures 5A, 5B:
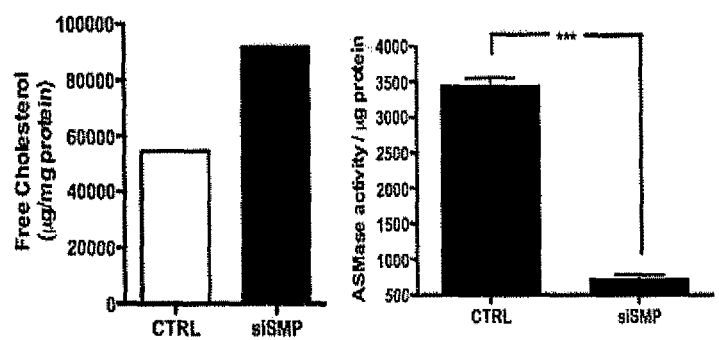
FIG. 5A-FIG. 5B: Shows that SMPDL-3b deficiency is associated with increased cellular cholesterol and decreased ASMase activity.

SMPDL-3b affects both cellular cholesterol (as shown in FIG. 5A) and sphingolipid (ASMase as shown in FIG. 5B). Therefore, modulation of SMPDL-3b per se or of cellular lipid through other agents such as cyclodextrin derivatives may represent a new strategy to prevent and treat proteinuric kidney disease through the modulation of cellular lipid content.

Figure 6A:
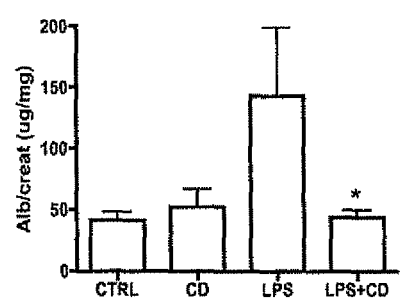
FIG. 6A-FIG. 6B: Depicts that CD partially prevents LPS induced podocyte damage.

Example 6—Methods of Lowering Plasma Membrane and Cellular Cholesterol for the Prevention, Treatment, Cure or Reversal of Renal-Related Disorders Referring to FIG. 6A, the antiproteinuric effects of CD were tested in an established experimental model of LPS induced proteinuria. Three mice per group were utilized. Mice were left untreated (CTRL), or received one injection of 4000 mg/kg Hydroxypropyl-beta-cyclodextrin (CD), or two injections of 200 µg LPS 24 hours apart (LPS), or received 4000 mg/kg of CD 1 hour prior to LPS treatment (LPS+CD). Urines were collected at 30 hours after the first LPS injection and analyzed for albumin and creatinine content by ELISA. Albuminuria was determined as the ratio between albumin and creatinine (µg/mg). It was found that cholesterol depletion by intravenous injection of Hydroxypropyl-beta-cyclodextrin (CD) protects from Lipopolysaccharide (LPS) induced proteinuria in mice.

Figure 6B:
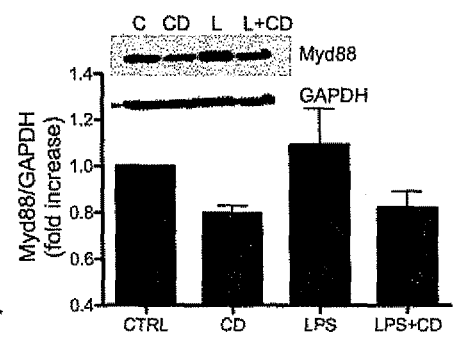

Referring to FIG. 6B, the antiproteinuric effects of CD as described in FIG. 6A were accompanied by a prevention of LPS-stimulated increase in MyD88 expression as determined by WB in isolated glomeruli, suggesting that CD may preserve podocyte function and thus prevent proteinuria in vivo.

Other Embodiments

Any improvement may be made in part or all of the assays, kits, and method steps. All references, including publications, patent applications, and patents, cited herein are hereby incorporated by reference. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. Although the experiments described herein pertain to diabetes and FSGS, the assays, method and kits described herein can be applied to any glomerular disease or disorder. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contraindicated by context.

What is claimed is:

1. A method of treating focal segmental glomerulosclerosis (FSGS) or Alport Syndrome (AS) in a subject in need thereof, comprising
administering to the subject a pharmaceutical composition comprising hydroxypropyl beta cyclodextrin as an active agent in a therapeutically effective amount for treating FSGS or AS.

2. The method of claim 1, wherein the composition is administered to the subject at one or more time points selected from the group consisting of: prior to kidney transplantation, during kidney transplantation, and subsequent to kidney transplantation.

3. The method of claim 1, wherein the composition further comprises a pharmaceutically acceptable carrier.

4. A method of reducing progression of FSGS, or recurrence of FSGS after kidney transplantation, or treating FSGS in a subject having FSGS, the method comprising
administering to the subject a composition comprising hydroxypropyl beta cyclodextrin as an active agent capable of at least one of: increasing SMPDL-3b levels in the subject, restoring cytoskeleton rearrangements in the subject, and decreasing or preventing B7-1 expression or activity in the subject,
wherein the composition is administered to the subject in an amount effective to reduce progression of FSGS or recurrence of FSGS after kidney transplantation, or to treat FSGS in the subject having FSGS.

5. The method of claim 4, wherein the composition is administered to the subject at one or more time points selected from the group consisting of: prior to kidney transplantation, during kidney transplantation, and subsequent to kidney transplantation.

6. The method of claim 4 wherein the composition further comprises a pharmaceutically acceptable carrier.

7. A method of treating focal segmental glomerulosclerosis (FSGS) or Alport Syndrome (AS) in a subject in need thereof, comprising administering to the subject a pharmaceutical composition comprising hydroxypropyl beta cyclodextrin as an active agent in an amount effective for reducing at least one of: plasma membrane cholesterol, plasma membrane lipids, cellular cholesterol, and cellular lipids in kidney cells of the subject.

8. The method of claim 7, wherein the composition is administered in an amount effective for preserving podocyte function and reducing or treating proteinuria in the subject.

9. The method of claim 7, wherein administration of the composition results in reduction of at least one of: plasma membrane cholesterol, plasma membrane lipids, cellular cholesterol, and cellular lipids in podocytes of the kidney of the subject.

10. The method of claim 7, wherein the composition is administered to the subject at one or more time points selected from the group consisting of: prior to kidney transplantation, during kidney transplantation, and subsequent to kidney transplantation.

11. The method of claim 7, wherein the composition further comprises a pharmaceutically acceptable carrier.

* * * * *

UNITED STATES PATENT AND TRADEMARK OFFICE
CERTIFICATE OF CORRECTION

PATENT NO. : 10,183,038 B2  
APPLICATION NO. : 14/967831  
DATED : January 22, 2019  
INVENTOR(S) : Alessia Fornoni Page 1 of 1

It is certified that error appears in the above-identified patent and that said Letters Patent is hereby corrected as shown below:

On the Title Page

Item (74) reads:
-- Attorney, Agent, or Firm – Millen, White, Zelano & Branigan, PC --
Should read:
-- Attorney, Agent, or Firm – Millen, White, Zelano & Branigan, PC; Ted W. Whitlock --

Signed and Sealed this
Twenty-third Day of July, 2019

Andrei Iancu
*Director of the United States Patent and Trademark Office*